US008748673B2

(12) United States Patent
Warner et al.

(10) Patent No.: US 8,748,673 B2
(45) Date of Patent: Jun. 10, 2014

(54) PROCESS OF RECOVERY OF ETHANOL FROM HYDROGENOLYSIS PROCESS

(75) Inventors: R. Jay Warner, Houston, TX (US); Wei Qi, Shijiazhuang (CN); Tatiana Sonnenberg, Houston, TX (US)

(73) Assignee: Celanese International Corporation, Dallas, TX (US)

( * ) Notice: Subject to any disclaimer, the term of this patent is extended or adjusted under 35 U.S.C. 154(b) by 244 days.

(21) Appl. No.: 13/299,816

(22) Filed: Nov. 18, 2011

(65) Prior Publication Data

US 2013/0131398 A1 May 23, 2013

(51) Int. Cl.
*C07C 67/08* (2006.01)
*C07C 29/149* (2006.01)

(52) U.S. Cl.
USPC ............................ 568/884; 568/885; 560/231

(58) Field of Classification Search
CPC ....................................................... C07C 67/08
USPC ............................ 568/884, 885; 560/231, 232
See application file for complete search history.

(56) References Cited

U.S. PATENT DOCUMENTS

| | | |
|---|---|---|
| 1,469,447 A | 10/1923 | Schneible |
| 1,939,116 A | 12/1933 | Fuchs |
| 2,591,671 A | 4/1952 | Catterall et al. |
| 2,591,672 A | 4/1952 | Catterall et al. |
| 2,607,719 A | 8/1952 | Eliot et al. |
| 2,702,783 A | 2/1955 | Harrison et al. |
| 2,715,604 A | 8/1955 | Weaver, Jr. |
| 2,744,939 A | 5/1956 | Kennel |
| 2,801,209 A | 7/1957 | Muller et al. |
| 3,404,186 A | 10/1968 | Bailey et al. |
| 3,408,267 A | 10/1968 | Miller et al. |
| 3,445,345 A | 5/1969 | Katzen et al. |
| 3,884,981 A | 5/1975 | Kiff |
| 3,925,490 A | 12/1975 | Reich et al. |
| 3,990,952 A | 11/1976 | Katzen et al. |
| 4,262,154 A | 4/1981 | Gane et al. |
| 4,306,942 A | 12/1981 | Brush et al. |
| 4,328,375 A | 5/1982 | Barlow |
| 4,338,221 A | 7/1982 | Qualeatti |
| 4,352,947 A | 10/1982 | Habib et al. |
| 4,370,491 A | 1/1983 | Bott et al. |
| 4,379,028 A | 4/1983 | Berg et al. |
| 4,395,576 A | 7/1983 | Kwantes et al. |
| 4,398,039 A | 8/1983 | Pesa et al. |
| 4,409,405 A | 10/1983 | Lin et al. |
| 4,421,939 A | 12/1983 | Kiff et al. |
| 4,422,903 A | 12/1983 | Messick et al. |
| 4,429,056 A | 1/1984 | Smith |
| 4,430,506 A | 2/1984 | Gauthier-Lafaye et al. |
| 4,443,639 A | 4/1984 | Pesa et al. |
| 4,448,644 A | 5/1984 | Foster et al. |
| 4,454,358 A | 6/1984 | Kummer et al. |
| 4,456,775 A | 6/1984 | Travers et al. |
| 4,476,326 A | 10/1984 | Lin et al. |
| 4,481,146 A | 11/1984 | Leupold et al. |
| 4,497,967 A | 2/1985 | Wan |
| 4,514,521 A | 4/1985 | Smith |
| 4,517,391 A | 5/1985 | Schuster et al. |
| 4,541,897 A | 9/1985 | Sommer et al. |
| 4,600,571 A | 7/1986 | McCarroll et al. |
| 4,611,085 A | 9/1986 | Kitson |
| 4,628,130 A | 12/1986 | Bournonville et al. |
| 4,678,543 A | 7/1987 | Houben et al. |
| 4,751,334 A | 6/1988 | Turner et al. |
| 4,758,600 A | 7/1988 | Arimitsu et al. |
| 4,761,505 A | 8/1988 | Diana et al. |
| 4,774,365 A | 9/1988 | Chen et al. |
| 4,837,367 A | 6/1989 | Gustafson et al. |
| 4,837,368 A | 6/1989 | Gustafson et al. |
| 4,842,693 A | 6/1989 | Wheldon |
| 4,943,354 A | 7/1990 | Osterburg et al. |
| 4,985,572 A | 1/1991 | Kitson et al. |
| 5,004,845 A | 4/1991 | Bradley et al. |
| 5,035,776 A | 7/1991 | Knapp |
| 5,047,592 A | 9/1991 | Carpenter |
| 5,061,671 A | 10/1991 | Kitson et al. |
| 5,124,004 A | 6/1992 | Grethlein et al. |
| 5,149,680 A | 9/1992 | Kitson et al. |
| 5,185,476 A | 2/1993 | Gustafson |
| 5,185,481 A | 2/1993 | Muto et al. |
| 5,196,601 A | 3/1993 | Kitsuki et al. |

(Continued)

FOREIGN PATENT DOCUMENTS

| | | |
|---|---|---|
| CA | 1233484 | 3/1988 |
| CN | 201768393 | 3/2011 |

(Continued)

OTHER PUBLICATIONS

Pallasana et al., Reaction Paths in the Hydrogenolysis of Acetic Acid to Ethanol over Pd(111), Re(0001), and RdRe Alloys, Journal of Catalysis 209, 289-305 Mar. 1, 2002.
Zhang et al. Hydrogenation of Ethyl Acetate to Ethanol over Ni-Based Catalysts Obtained from Ni/Al Hydrotalcite-Like Compounds. Molecules 2010, 15, 5139-5152, 2010.
International Search Report and Written Opinion mailed Mar. 7, 2013 in corresponding International Application No. PCT/US2012/064934.
International Search Report and Written Opinion for PCT/US2011/023338 mailed Sep. 6, 2011.
Juran et al., "Convert methanol to ethanol", Hydrocarbon Processing, Oct. 1985, pp. 85-87.
Subramani et al., "A Review of Recent Literature to Search for an Efficient Catalytic Process for the Conversion of Syngas to Ethanol", Energy & Fuels 2008, 22, pp. 814-839.

(Continued)

Primary Examiner — Yong Chu

(57) ABSTRACT

Disclosed herein are processes for alcohol production by reducing an esterification product, such as ethyl acetate. The processes comprise esterifying acetic acid and an alcohol such as ethanol to produce an esterification product. The esterification product is reduced with hydrogen in the presence of a catalyst to obtain a crude reaction mixture comprising ethyl acetate, ethanol, and at least one alcohol having at least 4 carbon atoms. The ethanol is recovered with a reduced amount of the alcohol having at least 4 carbon atoms.

27 Claims, 13 Drawing Sheets

(56) References Cited

U.S. PATENT DOCUMENTS

| | | |
|---|---|---|
| 5,198,592 A | 3/1993 | van Beijnum et al. |
| 5,215,902 A | 6/1993 | Tedder |
| 5,220,020 A | 6/1993 | Buchwald et al. |
| 5,250,271 A | 10/1993 | Horizoe et al. |
| 5,284,983 A | 2/1994 | Muto et al. |
| 5,334,751 A | 8/1994 | Lemanski et al. |
| 5,403,962 A | 4/1995 | Schneider et al. |
| 5,414,161 A | 5/1995 | Uhm et al. |
| 5,426,246 A | 6/1995 | Nagahara et al. |
| 5,449,440 A | 9/1995 | Rescalli et al. |
| 5,476,974 A | 12/1995 | Moore et al. |
| 5,480,665 A | 1/1996 | Smith |
| 5,488,185 A | 1/1996 | Ramachandran et al. |
| 5,502,094 A | 3/1996 | Moore et al. |
| 5,502,248 A | 3/1996 | Funk et al. |
| 5,565,068 A | 10/1996 | Parker et al. |
| 5,567,765 A | 10/1996 | Moore et al. |
| 5,658,962 A | 8/1997 | Moore et al. |
| 5,747,486 A | 5/1998 | Sohda et al. |
| 5,770,761 A | 6/1998 | Lin et al. |
| 5,831,133 A | 11/1998 | Mimoun |
| 5,993,610 A | 11/1999 | Berg |
| 5,998,658 A | 12/1999 | Wu et al. |
| 6,024,176 A | 2/2000 | Moore et al. |
| 6,046,127 A | 4/2000 | Mimoun |
| 6,093,845 A | 7/2000 | Van Acker et al. |
| 6,121,497 A | 9/2000 | Murphy |
| 6,204,299 B1 | 3/2001 | Moore et al. |
| 6,214,253 B1 | 4/2001 | Moore et al. |
| 6,361,713 B1 | 3/2002 | Moore et al. |
| 6,375,807 B1 | 4/2002 | Nieuwoudt et al. |
| 6,403,840 B1 | 6/2002 | Zhou et al. |
| 6,462,231 B1 | 10/2002 | Yanagawa et al. |
| 6,462,243 B1 | 10/2002 | Zhou et al. |
| 6,465,696 B1 | 10/2002 | Zhou et al. |
| 6,465,699 B1 | 10/2002 | Grosso |
| 6,472,572 B1 | 10/2002 | Zhou et al. |
| 6,486,368 B1 | 11/2002 | Zhou et al. |
| 6,491,983 B2 | 12/2002 | Moore et al. |
| 6,509,180 B1 | 1/2003 | Verser et al. |
| 6,525,230 B2 | 2/2003 | Grosso |
| 6,552,220 B1 | 4/2003 | Obana et al. |
| 6,623,330 B2 | 9/2003 | Fukuroi |
| 6,693,213 B1 | 2/2004 | Kolena et al. |
| 6,713,655 B2 | 3/2004 | Yilmaz et al. |
| 6,765,110 B2 | 7/2004 | Warner et al. |
| 6,768,021 B2 * | 7/2004 | Horan et al. ............... 560/265 |
| 6,809,217 B1 | 10/2004 | Colley et al. |
| 6,863,211 B2 | 3/2005 | Moore et al. |
| 6,867,164 B2 | 3/2005 | Obana et al. |
| 6,927,048 B2 | 8/2005 | Verser et al. |
| 7,019,182 B2 | 3/2006 | Grosso |
| 7,074,603 B2 | 7/2006 | Verser et al. |
| 7,091,155 B2 | 8/2006 | Inui et al. |
| 7,148,390 B2 | 12/2006 | Zhou et al. |
| 7,161,050 B2 | 1/2007 | Sherman et al. |
| 7,230,150 B2 | 6/2007 | Grosso et al. |
| 7,351,559 B2 | 4/2008 | Verser et al. |
| 7,361,794 B2 | 4/2008 | Grosso |
| 7,507,562 B2 | 3/2009 | Verser et al. |
| 7,553,397 B1 | 6/2009 | Colley et al. |
| 7,572,353 B1 | 8/2009 | Vander et al. |
| 7,594,981 B2 | 9/2009 | Ikeda |
| 7,608,744 B1 | 10/2009 | Johnston et al. |
| 7,652,167 B2 | 1/2010 | Miller et al. |
| 7,667,068 B2 | 2/2010 | Miller et al. |
| 7,682,812 B2 | 3/2010 | Verser et al. |
| 7,732,173 B2 | 6/2010 | Mairal et al. |
| 7,744,727 B2 | 6/2010 | Blum et al. |
| 7,790,938 B2 | 9/2010 | Kawasaki et al. |
| 7,838,708 B2 | 11/2010 | Sherman et al. |
| 7,842,844 B2 | 11/2010 | Atkins |
| 7,863,489 B2 | 1/2011 | Johnston et al. |
| 7,884,253 B2 | 2/2011 | Stites et al. |
| 7,888,082 B2 | 2/2011 | Verser et al. |
| 7,947,746 B2 | 5/2011 | Daniel et al. |
| 7,964,379 B2 | 6/2011 | Verser et al. |
| 8,002,953 B2 | 8/2011 | Lee et al. |
| 8,053,610 B2 | 11/2011 | Kikuchi et al. |
| 8,062,482 B2 | 11/2011 | Warner |
| 8,080,684 B2 | 12/2011 | Hassan et al. |
| 8,088,832 B2 | 1/2012 | Melnichuk et al. |
| 8,129,436 B2 | 3/2012 | Tirtowidjojo et al. |
| 8,198,057 B2 | 6/2012 | Padgett |
| 8,288,596 B2 | 10/2012 | Garton et al. |
| 8,299,132 B2 | 10/2012 | Gracey et al. |
| 8,299,133 B2 | 10/2012 | Gracey et al. |
| 2001/0027172 A1 | 10/2001 | Moore et al. |
| 2002/0156328 A1 | 10/2002 | Grosso |
| 2002/0198416 A1 | 12/2002 | Zhou et al. |
| 2003/0069452 A1 | 4/2003 | Sherman et al. |
| 2003/0077771 A1 | 4/2003 | Verser et al. |
| 2003/0078456 A1 | 4/2003 | Yilmaz et al. |
| 2003/0104587 A1 | 6/2003 | Verser et al. |
| 2003/0120121 A1 | 6/2003 | Sherman et al. |
| 2003/0125585 A1 | 7/2003 | Yilmaz et al. |
| 2003/0125589 A1 | 7/2003 | Grosso |
| 2003/0135069 A1 | 7/2003 | Fujita et al. |
| 2003/0153059 A1 | 8/2003 | Pilkington et al. |
| 2003/0166973 A1 | 9/2003 | Zhou et al. |
| 2004/0006246 A1 | 1/2004 | Sherman et al. |
| 2004/0063184 A1 | 4/2004 | Grichko |
| 2004/0152915 A1 | 8/2004 | Fujita et al. |
| 2004/0195084 A1 | 10/2004 | Hetherington et al. |
| 2004/0242917 A1 | 12/2004 | Inui et al. |
| 2004/0267074 A1 | 12/2004 | Grosso et al. |
| 2005/0043572 A1 | 2/2005 | Grosso |
| 2005/0192468 A1 | 9/2005 | Sherman et al. |
| 2005/0214408 A1 | 9/2005 | Pilkington et al. |
| 2006/0019360 A1 | 1/2006 | Verser et al. |
| 2006/0127999 A1 | 6/2006 | Verser et al. |
| 2006/0224013 A1 | 10/2006 | Inui et al. |
| 2006/0252956 A1 | 11/2006 | Miller et al. |
| 2007/0144886 A1 | 6/2007 | Sylvester et al. |
| 2007/0265360 A1 | 11/2007 | Luo et al. |
| 2008/0135396 A1 | 6/2008 | Blum |
| 2009/0005588 A1 | 1/2009 | Hassan et al. |
| 2009/0023192 A1 | 1/2009 | Verser et al. |
| 2009/0081749 A1 | 3/2009 | Verser et al. |
| 2009/0166172 A1 | 7/2009 | Casey et al. |
| 2009/0264285 A1 | 10/2009 | Luo et al. |
| 2010/0030002 A1 | 2/2010 | Johnston et al. |
| 2010/0069515 A1 | 3/2010 | Tirtowidjojo et al. |
| 2010/0080736 A1 | 4/2010 | Hassan et al. |
| 2010/0121119 A1 | 5/2010 | Sherman et al. |
| 2010/0185021 A1 | 7/2010 | Ross et al. |
| 2010/0261800 A1 | 10/2010 | Daniel et al. |
| 2010/0273229 A1 | 10/2010 | Verser et al. |
| 2010/0311138 A1 | 12/2010 | Padget |
| 2011/0004034 A1 | 1/2011 | Daniel et al. |
| 2011/0034741 A1 | 2/2011 | Sherman et al. |
| 2011/0046421 A1 | 2/2011 | Daniel et al. |
| 2011/0224462 A1 | 9/2011 | Ditzel et al. |
| 2013/0131198 A1 * | 5/2013 | Warner et al. ............... 518/702 |
| 2013/0131393 A1 | 5/2013 | Warner et al. |
| 2013/0131394 A1 * | 5/2013 | Warner et al. ............... 568/884 |
| 2013/0131395 A1 * | 5/2013 | Warner et al. ............... 568/884 |
| 2013/0131396 A1 * | 5/2013 | Warner et al. ............... 568/885 |
| 2013/0131397 A1 * | 5/2013 | Warner et al. ............... 568/885 |
| 2013/0131400 A1 | 5/2013 | Duff et al. |
| 2013/0158297 A1 | 6/2013 | Johnson et al. |
| 2013/0158302 A1 | 6/2013 | Duff et al. |

FOREIGN PATENT DOCUMENTS

| | | |
|---|---|---|
| CN | 102091429 | 6/2011 |
| CN | 101525272 | 5/2012 |
| CN | 202214306 | 5/2012 |
| DE | 2723611 | 11/1978 |
| DE | 60025239 | 6/2006 |
| EP | 0137749 | 4/1985 |
| EP | 0104197 | 5/1986 |
| EP | 0 992 484 A1 | 4/2000 |
| EP | 0990638 | 4/2000 |

(56) References Cited

FOREIGN PATENT DOCUMENTS

| | | |
|---|---|---|
| EP | 0944572 B1 | 4/2002 |
| EP | 2060553 | 5/2009 |
| JP | 2215790 | 8/1990 |
| JP | 5186391 | 7/1993 |
| JP | 6009454 | 1/1994 |
| JP | 6025033 | 2/1994 |
| JP | 6128181 | 5/1994 |
| JP | 2009-263356 | 11/2009 |
| JP | 2010-159212 | 7/2010 |
| WO | WO 82/03854 | 11/1982 |
| WO | WO 83/03409 | 10/1983 |
| WO | WO 98/25876 | 6/1998 |
| WO | WO 2008/135192 | 11/2008 |
| WO | WO 2009/009320 | 1/2009 |
| WO | WO 2009/009322 | 1/2009 |
| WO | WO 2009/009323 | 1/2009 |
| WO | WO 2009/063174 | 5/2009 |
| WO | WO 2009/063176 | 5/2009 |
| WO | WO 2009063176 A1 * | 5/2009 |
| WO | WO 2009/077719 | 6/2009 |
| WO | WO 2009/077720 | 6/2009 |
| WO | WO 2009/077725 | 6/2009 |
| WO | WO 2009/077729 | 6/2009 |
| WO | WO 2010/055285 | 5/2010 |
| WO | WO 2013/019236 A1 | 2/2013 |

\* cited by examiner

US 8,748,673 B2

PROCESS OF RECOVERY OF ETHANOL FROM HYDROGENOLYSIS PROCESS

FIELD OF THE INVENTION

The present invention relates generally to alcohol production from an esterification product, and in particular to producing ethanol through reducing an esterification product obtained by esterifying acetic acid.

BACKGROUND OF THE INVENTION

Ethanol for industrial use is conventionally produced from petrochemical feed stocks, such as oil, natural gas, or coal, from feed stock intermediates, such as syngas, or from starchy materials or cellulose materials, such as corn or sugar cane. Conventional methods for producing ethanol from petrochemical feed stocks, as well as from cellulose materials, include the acid-catalyzed hydration of ethylene, methanol homologation, direct alcohol synthesis, and Fischer-Tropsch synthesis. Instability in petrochemical feed stock prices contributes to fluctuations in the cost of conventionally produced ethanol, making the need for alternative sources of ethanol production all the greater when feed stock prices rise. Starchy materials, as well as cellulose material, are converted to ethanol by fermentation. However, fermentation is typically used for consumer production of ethanol, which is suitable for fuels or human consumption. In addition, fermentation of starchy or cellulose materials competes with food sources and places restraints on the amount of ethanol that can be produced for industrial use.

Ethanol production via the reduction of alkanoic acids and/or other carbonyl group-containing compounds, including esters, has been widely studied, and a variety of combinations of catalysts, supports, and operating conditions have been mentioned in the literature. Copper-iron catalysts for hydrogenolyzing esters to alcohols are described in U.S. Pat. No. 5,198,592. A hydrogenolysis catalyst comprising nickel, tin, germanium and/or lead is described in U.S. Pat. No. 4,628,130. A rhodium hydrogenolysis catalyst that also contains tin, germanium and/or lead is described in U.S. Pat. No. 4,456,775.

Several processes that produce ethanol from acetates, including methyl acetate and ethyl acetate, are known in the literature.

WO8303409 describes producing ethanol by carbonylation of methanol by reaction with carbon monoxide in the presence of a carbonylation catalyst to form acetic acid which is then converted to an acetate ester followed by hydrogenolysis of the acetate ester formed to give ethanol or a mixture of ethanol and another alcohol which can be separated by distillation. Preferably the other alcohol or part of the ethanol recovered from the hydrogenolysis step is recycled for further esterification. Carbonylation can be effected using a CO/$H_2$ mixture and hydrogenolysis can similarly be conducted in the presence of carbon monoxide, leading to the possibility of circulating gas between the carbonylation and hydrogenolysis zones with synthesis gas, preferably a 2:1 $H_2$:CO molar mixture being used as makeup gas.

WO2009063174 describes a continuous process for the production of ethanol from a carbonaceous feedstock. The carbonaceous feedstock is first converted to synthesis gas which is then converted to ethanoic acid, which is then esterified and which is then hydrogenated to produce ethanol.

WO2009009320 describes an indirect route for producing ethanol. Carbohydrates are fermented under homoacidogenic conditions to form acetic acid. The acetic acid is esterified with a primary alcohol having at least 4 carbon atoms and hydrogenating the ester to form ethanol.

US Pub. No. 20110046421 describes a process for producing ethanol comprising converting carbonaceous feedstock to syngas and converting the syngas to methanol. Methanol is carbonylated to ethanoic acid, which is then subjected to a two stage hydrogenation process. First the ethanoic acid is converted to ethyl ethanoate followed by a secondary hydrogenation to ethanol.

US Pub. No. 20100273229 describes a process for producing acetic acid intermediate from carbohydrates, such as corn, using enzymatic milling and fermentation steps. The acetic acid intermediate is acidified with calcium carbonate and the acetic acid is esterified to produce esters. Ethanol is produced by a hydrogenolysis reaction of the ester.

U.S. Pat. No. 7,884,253 describes a process for producing ethanol by converting syngas to methanol and catalytically converting the methanol into acetic acid. The acetic acid along with methanol is esterified to generate an acetate. The acetate is reduced with hydrogen to produce ethanol.

U.S. Pat. No. 5,414,161 describes a process for producing ethanol by a gas phase carbonylation of methanol with carbon monoxide followed by a hydrogenation. The carbonylation produces acetic acid and methyl acetate, which are separated and the methyl acetate is hydrogenated to produce ethanol in the presence of a copper-containing catalyst.

U.S. Pat. No. 4,497,967 describes a process for producing ethanol from methanol by first esterifying the methanol with acetic acid. The methyl acetate is carbonylated to produce acetic anhydride which is then reacted with one or more aliphatic alcohols to produce acetates. The acetates are hydrogenated to produce ethanol and one or more aliphatic alcohols. The one or more aliphatic alcohols formed during hydrogenation are returned to the acetic anhydride esterification reaction.

U.S. Pat. No. 4,454,358 describes a process for producing ethanol from methanol. Methanol is carbonylated to produce methyl acetate and acetic acid. The methyl acetate is recovered and hydrogenated to produce methanol and ethanol. Ethanol is recovered by separating the methanol/ethanol mixture. The separated methanol is returned to the carbonylation process.

The need remains for improved processes for efficient ethanol production by reducing esters on a commercially feasible scale.

SUMMARY OF THE INVENTION

In a first embodiment, the present invention is directed to a method of producing ethanol comprising esterifying acetic acid and ethanol in a first reaction zone to produce an ester feed stream, reacting at least a portion of the ester feed stream with hydrogen in a second reaction zone to produce a crude reaction mixture comprising ethyl acetate, ethanol, and at least one alcohol having at least 4 carbon atoms, separating at least a portion of the crude reaction mixture in a first distillation column to yield a first distillate comprising ethyl acetate and a first residue comprising ethanol, and separating at least a portion of the first residue in a second distillation column to yield an ethanol sidestream and a second residue comprising the at least one alcohol having at least 4 carbon atoms.

In a second embodiment, the present invention is directed to a method of producing ethanol comprising esterifying acetic acid and ethanol in a first reaction zone to produce an ester feed stream, reacting at least a portion of the ester feed stream with hydrogen in a second reaction zone to produce a crude reaction mixture, wherein the conversion of ethyl acetate to ethanol is less than 85%, separating at least a portion of the crude reaction mixture in a first distillation column to yield a first distillate comprising ethyl acetate and ethanol, and a first residue comprising ethanol, and returning the distillate to the second reaction zone.

In a third embodiment, the present invention is directed to a method of producing ethanol comprising esterifying acetic acid and ethanol in a first reaction zone to produce an ester feed stream, reacting at least a portion of the ester feed stream with hydrogen in a second reaction zone to produce a crude reaction mixture, wherein the conversion of ethyl acetate to ethanol is greater than 85%, separating at least a portion of the crude reaction mixture in a first distillation column to yield a first distillate comprising ethyl acetate and ethanol, and a first residue comprising ethanol and at least one alcohol having at least 4 carbon atoms, and returning the first distillate to the first reaction zone.

In a fourth embodiment, the present invention is directed to a method of producing ethanol comprising esterifying acetic acid and ethanol in a first reaction zone to produce an ester feed stream, reacting at least a portion of the ester feed stream with hydrogen in a second reaction zone to produce a crude reaction mixture comprising ethanol, diethyl acetal, and at least one alcohol having at least 4 carbon atoms, and separating at least a portion of the crude reaction mixture in one or more distillation columns to yield an ethanol product, wherein the ethanol product, based on the crude reaction mixture, has a reduced amount of diethyl acetal and a reduced amount of the at least one alcohol having at least 4 carbon atoms.

In a fifth embodiment, the present invention is directed to a method of producing ethanol esterifying acetic acid and ethanol in a first reaction zone to produce an ester feed stream, reacting at least a portion of the ester feed stream with hydrogen in a second reaction zone to produce a crude reaction mixture, and separating at least a portion of the crude hydrogenation product in a first distillation column operated at a pressure of less than 101 kPa to yield a first distillate comprising ethyl acetate and ethanol and a residue comprising ethanol.

BRIEF DESCRIPTION OF DRAWINGS

The invention is described in detail below with reference to the appended drawings, wherein like numerals designate similar parts.

DETAILED DESCRIPTION OF THE INVENTION

Introduction

The present invention relates to methods for producing ethanol from acetic acid through an acetate intermediate. In particular, the method involves esterifying ethanol and acetic acid to produce an esterification product, producing a crude ethanol mixture from the esterification product via hydrogenolysis, and separating at least a portion of the crude ethanol mixture in one or more distillation columns to yield an ethanol product, wherein the ethanol product, based on the crude ethanol mixture, has a reduced amount of at least one alcohol having at least 4 carbon atoms. The method of the present invention involves at least two different reactions that may form minor amounts of impurities such as higher alcohols and acetals. "Higher alcohols" refers to alcohols with at least 4 carbon atoms. In a preferred embodiment, the alcohol has 4 carbons. The inventors have recognized the previously unknown problem that these higher alcohols may build up in ethanol-producing processes through recycled streams, reducing the efficiency of ethanol production. The present invention advantageously removes these higher alcohols from the crude ethanol mixture in one or more distillation columns to produce an ethanol product that has a reduced amount of higher alcohols than the hydrogenolysis product and is capable of being efficiently recycled. In addition, the present invention provides efficient separation processes for recovering ethanol after the hydrogenolysis of ethyl acetate.

Figure 1B:
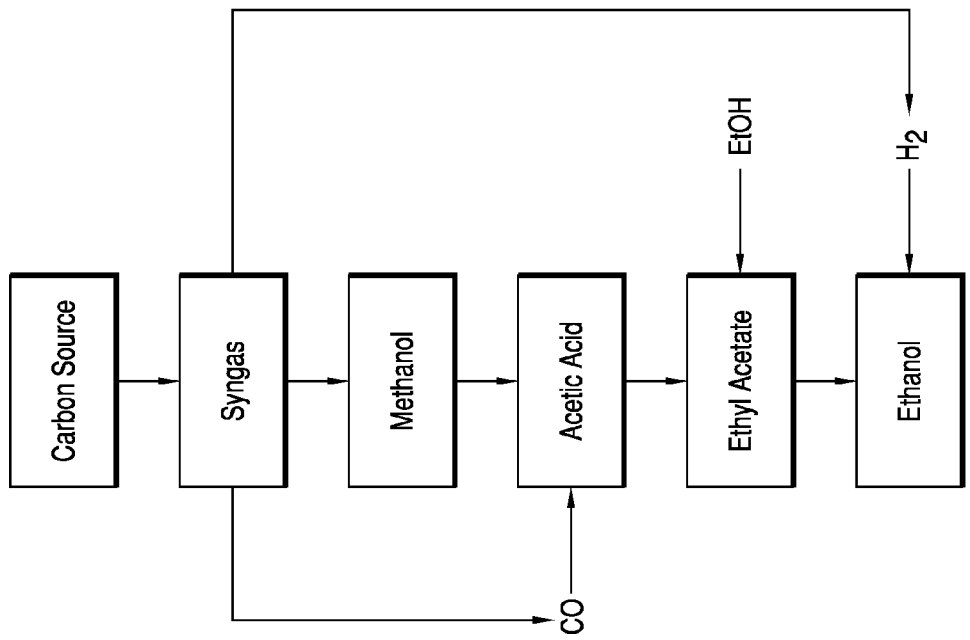
FIGS. 1A and 1B are general flow schemes for producing ethanol from a carbon source in accordance with one embodiment of the present invention.
Figure 1A:
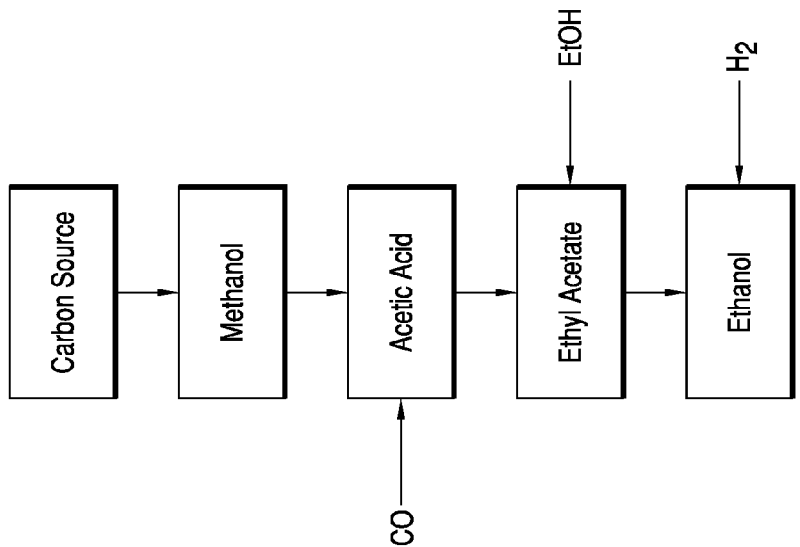

The embodiments of the present invention may also be integrated with methods for producing acetic acid and/or methods for producing ethanol as shown in FIGS. 1A and 1B. For example, acetic acid may be produced from methanol, and thus ethanol production according to embodiments of the present invention may be produced from methanol. In one embodiment, the present invention comprises producing ethanol from methanol by carbonylating the methanol to form acetic acid, esterifying the acetic acid along with ethanol to form an ester, and reducing the ester to form an ethanol product. In yet another embodiment, the present invention comprises producing methanol from syngas, carbonylating the methanol to form acetic acid, esterifying the acetic acid to form an ester, and reducing the ester to an alcohol, namely ethanol. In still another embodiment, the present invention comprises producing ethanol from a carbon source, such as coal, biomass, petroleum, or natural gas, by converting the carbon source to syngas, followed by converting the syngas to methanol, carbonylating the methanol to form acetic acid, esterifying the acetic acid to form an ester, and reducing the ester to an alcohol. In still another embodiment, the present invention comprises producing ethanol from a carbon source, such as coal, biomass, petroleum, or natural gas, by converting the carbon source to syngas, separating the syngas into a hydrogen stream and a carbon monoxide stream, carbonylating a methanol with the carbon monoxide stream to form acetic acid, esterifying the acetic acid to form an ester, and reducing the ester to an alcohol. These reactions, that is, the production of syngas from a carbonaceous source, the production of methanol from syngas or carbonaceous source, the carbonylation of methanol, the esterification of acetic acid and ethanol, and the reduction of the ester, may all form by-products which may produce higher alcohols in ethanol producing processes.

In particular, embodiments of the present invention are directed to methods for ethanol production from hydrogenolysis which reduce the buildup of higher alcohols through the use of one or more distillation columns. Higher alcohols may build up when a stream is recycled within an ethanol producing process. In one embodiment, at least a portion of the ethanol product may be recycled. In another embodiment, the ethanol product may be dried before being recycled. In yet another embodiment, a drier ethanol product stream and a wetter ethanol product stream may be produced, and either or a portion of both may be recycled. In yet another embodiment, a stream comprising ethanol and ethyl acetate may be recycled. In another embodiment, any of these recycled streams may be combined with the acetic acid and esterified to form ethyl acetate.

Embodiments of the present invention are also directed to methods for ethanol production from hydrogenolysis which reduce the buildup of higher alcohols and remove acetals through the use of one or more distillation columns. In one embodiment, acetals such as ethyl acetate are removed in an overhead stream of a distillation column. In another embodiment, ethyl acetate is removed as an overhead stream and higher alcohols are removed as a residue in a distillation column.

I. Esterification

The esterification reactants, acids and alcohols, used in connection with the process of this invention may be derived from any suitable source including carbon source such as natural gas, petroleum, coal, biomass, and so forth. Acetic acid may be produced by several methods, including but not limited to, methanol carbonylation, acetaldehyde oxidation, ethylene oxidation, oxidative fermentation, and anaerobic fermentation.

A. Acetic Acid Sources

1. Carbonylation

In one embodiment, the production of ethanol may be integrated with such methanol carbonylation processes. Methanol carbonylation processes suitable for production of acetic acid are described in U.S. Pat. Nos. 7,208,624; 7,115,772; 7,005,541; 6,657,078; 6,627,770; 6,143,930; 5,599,976; 5,144,068; 5,026,908; 5,001,259; and 4,994,608; the entire disclosures of which are incorporated herein by reference. A carbonylation system preferably comprises a reaction zone, which includes a reactor, a flasher and optionally a reactor recovery unit. In one embodiment, carbon monoxide is reacted with methanol in a suitable reactor, e.g., a continuous stirred tank reactor ("CSTR") or a bubble column reactor. Preferably, the carbonylation process is a low water, catalyzed, e.g., rhodium-catalyzed, carbonylation of methanol to acetic acid, as exemplified in U.S. Pat. No. 5,001,259, which is hereby incorporated by reference.

The carbonylation reaction may be conducted in a homogeneous catalytic reaction system comprising a reaction solvent, methanol and/or reactive derivatives thereof, a Group VIII catalyst, at least a finite concentration of water, and optionally an iodide salt.

Suitable catalysts include Group VIII catalysts, e.g., rhodium and/or iridium catalysts. When a rhodium catalyst is utilized, the rhodium catalyst may be added in any suitable form such that the active rhodium catalyst is a carbonyl iodide complex. Exemplary rhodium catalysts are described in Michael GauB, et al., *Applied Homogeneous Catalysis with Organometallic Compounds: A Comprehensive Handbook in Two Volumes*, Chapter 2.1, p. 27-200, ($1^{st}$ ed., 1996). Iodide salts optionally maintained in the reaction mixtures of the processes described herein may be in the form of a soluble salt of an alkali metal or alkaline earth metal or a quaternary ammonium or phosphonium salt. In certain embodiments, a catalyst co-promoter comprising lithium iodide, lithium acetate, or mixtures thereof may be employed. The salt co-promoter may be added as a non-iodide salt that will generate an iodide salt. The iodide catalyst stabilizer may be introduced directly into the reaction system. Alternatively, the iodide salt may be generated in-situ since under the operating conditions of the reaction system, a wide range of non-iodide salt precursors will react with methyl iodide or hydroiodic acid in the reaction medium to generate the corresponding co-promoter iodide salt stabilizer. For additional detail regarding rhodium catalysis and iodide salt generation, see U.S. Pat. Nos. 5,001,259; 5,026,908; and 5,144,068, which are hereby incorporated by reference.

When an iridium catalyst is utilized, the iridium catalyst may comprise any iridium-containing compound which is soluble in the liquid reaction composition. The iridium catalyst may be added to the liquid reaction composition for the carbonylation reaction in any suitable form which dissolves in the liquid reaction composition or is convertible to a soluble form. Examples of suitable iridium-containing compounds which may be added to the liquid reaction composition include: $IrCl_3$, $IrI_3$, $IrBr_3$, $[Ir(CO)_2I]_2$, $[Ir(CO)_2Cl]_2$, $[Ir(CO)_2Br]_2$, $[Ir(CO)_2I_2]^-H^+$, $[Ir(CO)_2Br_2]^-H^+$, $[Ir(CO)_2I_4]^-H^+$, $[Ir(CH_3)I_3(CO)_2)]^-H^+$, $Ir_4(CO)_{12}$, $IrCl_3.3H_2O$, $IrBr_3.3H_2O$, iridium metal, $Ir_2O_3$, $Ir(acac)(CO)_2$, $Ir(acac)_3$, iridium acetate, $[Ir_3O(OAc)_6(H_2O)_3][OAc]$, and hexachloroiridic acid $H_2IrCl_6$. Chloride-free complexes of iridium such as acetates, oxalates and acetoacetates are usually employed as starting materials. The iridium catalyst concentration in the liquid reaction composition may be in the range of 100 to 6000 wppm. The carbonylation of methanol utilizing iridium catalyst is well known and is generally described in U.S. Pat. Nos. 5,942,460; 5,932,764; 5,883,295; 5,877,348; 5,877,347 and 5,696,284, the entireties of which are hereby incorporated by reference.

A halogen co-catalyst/promoter is generally used in combination with the Group VIII metal catalyst component. Methyl iodide is a preferred halogen promoter. Preferably, the concentration of the halogen promoter in the reaction medium ranges from 1 wt. % to 50 wt. %, and more preferably from 2 wt. % to 30 wt. %.

The halogen promoter may be combined with the salt stabilizer/co-promoter compound. Particularly preferred are iodide or acetate salts, e.g., lithium iodide or lithium acetate.

Other promoters and co-promoters may be used as part of the catalytic system of the present invention as described in U.S. Pat. No. 5,877,348, which is hereby incorporated by reference. Suitable promoters are selected from ruthenium, osmium, tungsten, rhenium, zinc, cadmium, indium, gallium, mercury, nickel, platinum, vanadium, titanium, copper, aluminum, tin, antimony, and are more preferably selected from ruthenium and osmium. Specific co-promoters are described in U.S. Pat. No. 6,627,770, which is incorporated herein by reference.

A promoter may be present in an effective amount up to the limit of its solubility in the liquid reaction composition and/or any liquid process streams recycled to the carbonylation reactor from the acetic acid recovery stage. When used, the promoter is suitably present in the liquid reaction composition at a molar ratio of promoter to metal catalyst of 0.5:1 to 15:1, preferably 2:1 to 10:1, more preferably 2:1 to 7.5:1. A suitable promoter concentration is 400 to 5000 wppm.

In one embodiment, the temperature of the carbonylation reaction in the reactor is preferably from 150° C. to 250° C., e.g., from 150° C. to 225° C., or from 150° C. to 200° C. The pressure of the carbonylation reaction is preferably from 1 to 20 MPa, preferably 1 to 10 MPa, most preferably 1.5 to 5 MPa. Acetic acid is typically manufactured in a liquid phase reaction at a temperature from about 150° C. to about 200° C. and a total pressure from about 2 to about 5 MPa.

In one embodiment, reaction mixture comprises a reaction solvent or mixture of solvents. The solvent is preferably compatible with the catalyst system and may include pure alcohols, mixtures of an alcohol feedstock, and/or the desired carboxylic acid and/or esters of these two compounds. In one embodiment, the solvent and liquid reaction medium for the (low water) carbonylation process is preferably acetic acid.

Water may be formed in situ in the reaction medium, for example, by the esterification reaction between methanol reactant and acetic acid product. In some embodiments, water is introduced to the reactor together with or separately from the other components of the reaction medium. Water may be separated from the other components of the reaction product withdrawn from reactor and may be recycled in controlled amounts to maintain the required concentration of water in the reaction medium. Preferably, the concentration of water maintained in the reaction medium ranges from 0.1 wt. % to 16 wt. %, e.g., from 1 wt. % to 14 wt. %, or from 1 wt. % to 3 wt. % of the total weight of the reaction product.

The desired reaction rates are obtained even at low water concentrations by maintaining in the reaction medium an ester of the desired carboxylic acid and an alcohol, desirably the alcohol used in the carbonylation, and an additional iodide ion that is over and above the iodide ion that is present as hydrogen iodide. An example of a preferred ester is methyl acetate. The additional iodide ion is desirably an iodide salt, with lithium iodide (LiI) being preferred. It has been found, as described in U.S. Pat. No. 5,001,259, that under low water concentrations, methyl acetate and lithium iodide act as rate promoters only when relatively high concentrations of each of these components are present and that the promotion is higher when both of these components are present together. The absolute concentration of iodide ion is not a limitation on the usefulness of the present invention.

In low water carbonylation, the additional iodide over and above the organic iodide promoter may be present in the catalyst solution in amounts ranging from 2 wt. % to 20 wt. %, e.g., from 2 wt. % to 15 wt. %, or from 3 wt. % to 10 wt. %; the methyl acetate may be present in amounts ranging from 0.5 wt. % to 30 wt. %, e.g., from 1 wt. % to 25 wt. %, or from 2 wt. % to 20 wt. %; and the lithium iodide may be present in amounts ranging from 5 wt. % to 20 wt. %, e.g., from 5 wt. % to 15 wt. %, or from 5 wt. % to 10 wt. %. The catalyst may be present in the catalyst solution in amounts ranging from 200 wppm to 2000 wppm, e.g., from 200 wppm to 1500 wppm, or from 500 wppm to 1500 wppm.

Alternatively, acetic acid in vapor form may be taken directly as crude product from the flash vessel of a methanol carbonylation unit of the class described in U.S. Pat. No. 6,657,078, the entirety of which is incorporated herein by reference. The crude vapor product, for example, may be fed directly to the esterification reaction zone of the present invention without the need for condensing the acetic acid and light ends or removing water, saving overall processing costs.

2. Direct from Syngas

As petroleum and natural gas prices fluctuate becoming either more or less expensive, methods for producing acetic acid and intermediates such as methanol and carbon monoxide from alternate carbon sources have drawn increasing interest. In particular, when petroleum is relatively expensive, it may become advantageous to produce acetic acid from synthesis gas ("syngas") that is derived from more available carbon sources. U.S. Pat. No. 6,232,352, the entirety of which is incorporated herein by reference, for example, teaches a method of retrofitting a methanol plant for the manufacture of acetic acid. By retrofitting a methanol plant, the large capital costs associated with CO generation for a new acetic acid plant are significantly reduced or largely eliminated. All or part of the syngas is diverted from the methanol synthesis loop and supplied to a separator unit to recover CO, which is then used to produce acetic acid. In a similar manner, hydrogen for the hydrogenolysis step may be supplied from syngas.

In some embodiments, some or all of the raw materials may be derived partially or entirely from syngas. For example, the acetic acid may be formed from methanol and carbon monoxide, both of which may be derived from syngas. The syngas may be formed by partial oxidation reforming or steam reforming, and the carbon monoxide may be separated from syngas. Similarly, hydrogen that is used in the step of hydrogenating the ethyl acetate to form the crude reaction mixture may be separated from syngas. The syngas, in turn, may be derived from variety of carbon sources. The carbon source, for example, may be selected from the group consisting of natural gas, oil, petroleum, coal, biomass, and combinations thereof. Syngas or hydrogen may also be obtained from bio-derived methane gas, such as bio-derived methane gas produced by landfills or agricultural waste.

3. Fermentation to Acetic Acid

In another embodiment, the acetic acid used in the esterification may be formed from the fermentation of biomass. The fermentation process preferably utilizes an acetogenic process or a homoacetogenic microorganism to ferment sugars to acetic acid producing little, if any, carbon dioxide as a by-product. The carbon efficiency for the fermentation process preferably is greater than 70%, greater than 80% or greater than 90% as compared to conventional yeast processing, which typically has a carbon efficiency of about 67%. Optionally, the microorganism employed in the fermentation process is of a genus selected from the group consisting of *Clostridium, Lactobacillus, Moorella, Thermoanaerobacter, Propionibacterium, Propionispera, Anaerobiospirillum*, and *Bacteriodes*, and in particular, species selected from the group consisting of *Clostridium formicoaceticum, Clostridium butyricum, Moorella thermoacetica, Thermoanaerobacter kivui, Lactobacillus delbrukii, Propionibacte-*

*rium acidipropionici, Propionispera arboris, Anaerobiospirillum succinicproducens, Bacteriodes amylophilus* and *Bacteriodes ruminicola*. Optionally in this process, all or a portion of the unfermented residue from the biomass, e.g., lignans, may be gasified to form hydrogen that may be used in the hydrogenolysis step of the present invention. Exemplary fermentation processes for forming acetic acid are disclosed in U.S. Pat. Nos. 6,509,180; 6,927,048; 7,074,603; 7,507,562; 7,351,559; 7,601,865; 7,682,812; and 7,888,082, the entireties of which are incorporated herein by reference. See also U.S. Pub. Nos. 2008/0193989 and 2009/0281354, the entireties of which are incorporated herein by reference.

Examples of biomass include, but are not limited to, agricultural wastes, forest products, grasses, and other cellulosic material, timber harvesting residues, softwood chips, hardwood chips, tree branches, tree stumps, leaves, bark, sawdust, off-spec paper pulp, corn, corn stover, wheat straw, rice straw, sugarcane bagasse, switchgrass, miscanthus, animal manure, municipal garbage, municipal sewage, commercial waste, grape pumice, almond shells, pecan shells, coconut shells, coffee grounds, grass pellets, hay pellets, wood pellets, cardboard, paper, plastic, and cloth. See, e.g., U.S. Pat. No. 7,884,253, the entirety of which is incorporated herein by reference. Another biomass source is black liquor, a thick, dark liquid that is a byproduct of the Kraft process for transforming wood into pulp, which is then dried to make paper. Black liquor is an aqueous solution of lignin residues, hemicellulose, and inorganic chemicals.

U.S. Pat. No. RE 35,377, also incorporated herein by reference, provides a method for the production of methanol by conversion of carbonaceous materials such as oil, coal, natural gas and biomass materials. The process includes hydrogasification of solid and/or liquid carbonaceous materials to obtain a process gas which is steam pyrolized with additional natural gas to form synthesis gas. The syngas is converted to methanol which may be carbonylated to acetic acid. The method likewise produces hydrogen which may be used in connection with this invention as noted above. U.S. Pat. No. 5,821,111, which discloses a process for converting waste biomass through gasification into synthesis gas, and U.S. Pat. No. 6,685,754, which discloses a method for the production of a hydrogen-containing gas composition, such as a synthesis gas including hydrogen and carbon monoxide, are incorporated herein by reference in their entireties.

4. Acetic Acid Feed

The acetic acid feed stream that is fed to the esterification step may also comprise other carboxylic acids and anhydrides, acetaldehyde, and acetone. In one aspect, the acetic acid feed stream comprises one or more of the compounds selected from the group consisting of acetic acid, propionic acid, acetic anhydride, acetaldehyde, ethyl acetate, diethyl acetal, and mixtures thereof. These other compounds may also be hydrogenated in the processes of the present invention. Water may also be present, generally in amounts of less than 10 wt. %, in the acetic acid feed.

B. Ethanol Feed

The alcohol feed stream fed to the esterification step may comprise ethanol. Ethanol may be obtained from a widely used bio-fermentation process and/or wood pyrolysis. Ethanol may also be produced by hydrating ethylene. In some embodiments, ethanol may be obtained by reducing acetic acid with hydrogen to ethanol in the presence of a catalyst, as described in U.S. Pat. Nos. 7,863,489, and 7,608,744, the entire contents of which are hereby incorporated by reference.

In a preferred embodiment, a portion of the ethanol feed may be obtained from the products of the hydrogenolysis reactor. In one embodiment, at least a portion of the ethanol product may be recycled. In another embodiment, at least a portion of the ethanol product may be dried before being recycled. In yet another embodiment, a drier ethanol product stream and a wetter ethanol product stream may be produced, and either or a portion of both may be recycled. In yet another embodiment, a stream comprising ethanol and ethyl acetate may be recycled. In another embodiment, any of these recycled streams may be combined with the acetic acid and esterified to form ethyl acetate.

In one embodiment, the ethanol feed stream may comprise a reduced amount of higher alcohols and acetals, i.e., less than 0.5 wt. %, less than 0.1 wt. %, or less than 0.05 wt. %. In one embodiment, the ethanol feed stream may comprise low concentrations of water, e.g., less than 10 wt. % or less than 5 wt. %.

C. Esterification Reaction

Figure 2:
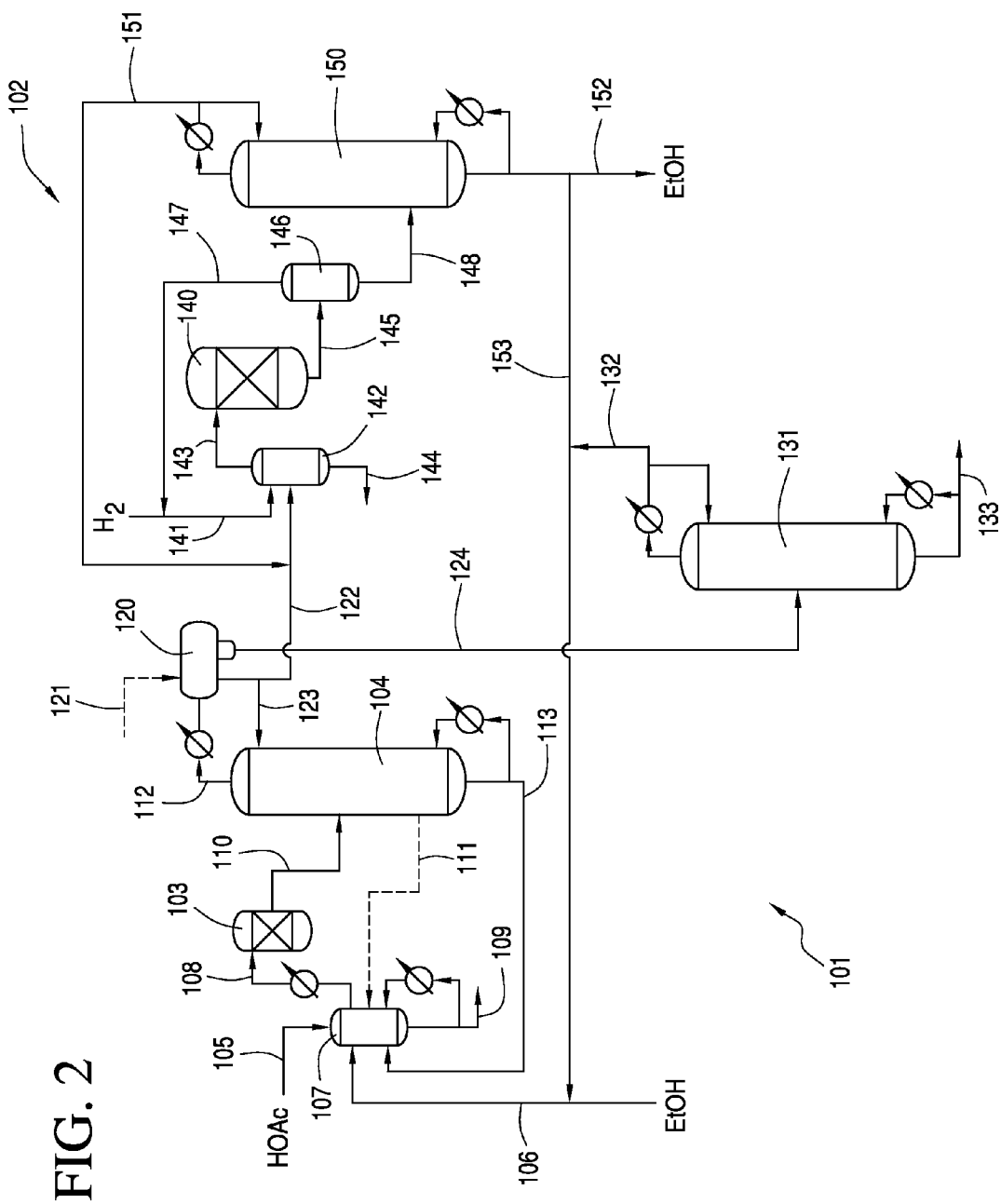
FIG. 2 is a schematic diagram of ethanol production process that directly feeds an organic phase of the esterification product produced by vapor esterification to the hydrogenolysis zone in accordance with one embodiment of the present invention.

The process of the present invention comprises an esterification zone 101 and a hydrogenolysis zone 102 as shown in FIG. 2. Esterification may be carried out in either the liquid or vapor phase. The process may be operated continuously or batchwise. Liquid phase esterification of acetic acid and ethanol has an equilibrium constant, $K_x$, of about 4, while vapor phase esterification of acetic acid and ethanol has a higher equilibrium constant, $K_x$, of about 30 at 130° C.

The formation of the esterification product in the esterification equilibrium reaction may be enhanced by the presence of a catalyst. A variety of homogeneous or heterogeneous acid catalysts may also be employed within the scope of this invention. The catalyst should be stable at the desired reaction temperature. Suitable catalysts include, without limitation, sulfuric acid, sulfonic acid, alkyl sulfonic acids, and aromatic sulfonic acids. Alkyl sulfonic and aromatic sulfonic acids may include methane sulfonic acid, benzene sulfonic acid and p-toluene sulfonic acid. In one embodiment, an ion exchange resin, e.g., Amberlyst™ 15, Amberlyst™ 36, Amberlyst™ 70, or Purolite™ CT179, may be used. Sulfuric acid, acidic zeolites, or heteropoly acids can also be used within the scope of the invention.

1. Ethanol to Acetic Acid Molar Ratio

In either the vapor or liquid phase reactions, although ethanol and acetic acid may be fed in equimolar amounts, in commercial ester production processes ethanol may be employed in excess molar amounts in the reaction mixture. In one aspect, because incomplete conversion of acetic acid in the esterification is less significant for purposes of the present invention, in some embodiments, it may be preferably to use an excess molar ratio of acetic acid. In one embodiment, the molar ratio of acetic acid to ethanol is greater than 1.01:1, e.g., greater than 1.05:1, greater than 1.2:1 or greater than 1.5:1. In terms of ranges, the molar ratio of acetic acid to ethanol may be from 1.01:1 to 5:1, e.g., from 1.01:1 to 3:1, from 1.05:1 to 3:1 or from 1.5:1 to 2.8:1. Without being bound by theory, the use of an excess molar amount of acetic acid, particularly under vapor phase esterification conditions, may desirably reduce formation of diethyl ether. A molar ratio that is greater than 1.5:1 under vapor phase conditions, at reaction temperatures of less than 130° C., may result in substantially no formation of diethyl ether.

Additionally, the use of excess acetic acid may allow for higher conversion rates of ethanol in the esterification reactor. In one embodiment, at least 75% of the ethanol fed to the esterification reactor is converted to ethyl acetate, e.g., at least 90% or at least 95%.

2. Vapor Phase

Vapor phase esterification may be carried out in a closely-coupled reactor 103 and distillation column 104 in the esterification zone 101 as shown in FIG. 2. Suitable reactors, in some embodiments, may include a variety of configurations using a fixed bed reactor or a fluidized bed reactor. In many embodiments of the present invention, an "adiabatic" reactor can be used; that is, there is little or no need for internal plumbing through the reaction zone to add or remove heat. In other embodiments, a radial flow reactor or reactors may be employed as the reactor, or a series of reactors may be employed with or without heat exchange, quenching, or introduction of additional feed material. Alternatively, a shell and tube reactor provided with a heat transfer medium may be used. In many cases, the reaction zone may be housed in a single vessel or in a series of vessels with heat exchangers therebetween. Reactor 103 may be a fixed-bed reactor and may comprise a heterogeneous catalyst.

In another embodiment, the reaction may be carried out in the vapor phase using a heterogeneous reactive distillation column. One or more reactors may be connected with the column.

Acetic acid feed stream in line 105 and ethanol feed stream in line 106, respectively, are fed to a vaporizer 107 to create a vapor feed stream in line 108 that is directed to reactor 103. In one embodiment, prior to feeding into vaporizer 107, the acetic acid feed stream and/or ethanol feed stream may be preheated. Vaporizer 107 may be fed with liquid reactants or vapor reactants, and preferably all the reactants are in the liquid phase. The acetic acid and ethanol may be vaporized at or near the reaction temperature. For reactions conducted in the vapor phase, the temperature should be controlled in the system such that it does not fall below the dew point of acetic acid. In one embodiment, the acetic acid may be vaporized at the boiling point of acetic acid at the particular pressure, and then the vaporized acetic acid may be further heated to the reactor inlet temperature. In another embodiment, the acetic acid is mixed with other gases before vaporizing, followed by heating the mixed vapors up to the reactor inlet temperature.

As shown in FIG. 2, acetic acid feed stream in line 105 may be fed to the top of vaporizer 107 and ethanol feed stream in line 106 may be fed at a point below the acetic acid feed stream point. The location of the feed points to vaporizer 107 may vary depending on the vessel configuration. Vaporizer 107 may be a vessel equipped with heat energy input sufficient to vaporize the liquid feed. The vessel may be jacketed, contain internal heating coils, or contain external thermosyphon, or forced circulation type reboilers. Optionally, lines 105 and 106 may be combined and jointly fed to vaporizer 107. Preferably, the vapor feed stream in line 108 is at a sufficient temperature to remain in the vapor phase. The temperature of the vapor feed stream in line 108 is preferably from 50° C. to 200° C., e.g., from 90° C. to 175° C. or from 100° C. to 170° C. In one embodiment, vapor feed stream 108 may be further preheated prior to being fed to reactor 103. The process may control the vapor-phase esterification reaction temperature by super-heating the vaporized feed in line 108 using a heat exchanger that is used to control the reactor inlet temperature.

Any feed that is not vaporized is removed from vaporizer 107 and may be recycled or discarded. In one embodiment, there may be a relatively small blowdown stream 109 that comprises heavy compounds that may be withdrawn from vaporizer 107. Blowdown stream 109 may be reboiled as necessary. The mass flow ratio of the vapor feed stream 108 to blowdown stream 109 may be greater than 5:1, e.g., greater than 50:1, or greater than 500:1. When ethanol from the hydrogenolysis zone 102 is recycled to the esterification zone 101, the ethanol may contain heavy compounds such as higher alcohols and/or higher acetates. These heavy compounds may buildup in the blowdown stream 109.

Although vaporizer 107 preferably comprises little or no acidic catalyst, due to the vaporization conditions, some acetic acid and ethanol may be esterified. Thus, vaporizer 107 may be a non-catalyzed reactor that produces ethyl acetate. Thus, vapor feed stream in line 108 in addition to containing acetic acid and ethanol, may also comprise minor amounts of ethyl acetate, e.g., in an amount of less than 15 wt. % based on the total weight of the vapor feed stream in line 108, e.g., less than 10 wt. % or less than 5 wt. %. In addition to the minor amounts of ethyl acetate, in one embodiment, vapor feed stream in line 108 may comprise a weight majority of acetic acid, e.g., at least 40 wt. %, at least 50 wt. % or at least 60 wt. %.

In one optional embodiment, there may be a liquid reactor (not shown) prior to vaporizer 107. The liquid reactor may contain a suitable acidic catalyst. Acetic acid feed stream in line 105 and ethanol feed stream in line 106 may be fed to the liquid reactor which produces an intermediate mixture that is vaporized. The additional feeds of acetic acid and ethanol may be fed with the intermediate mixture to vaporizer 107.

Vapor feed stream in line 108 is shown as being directed to the top of reactor 103 in FIG. 2, but in further embodiments, line 108 may be directed to the side, upper portion, or bottom of reactor 103. Reactor 103 contains the catalyst that is used in the esterification of acetic acid and ethanol. In one embodiment, one or more guard beds (not shown) may be used upstream of the reactor, optionally upstream of the vaporizer 107, to protect the catalyst from poisons or undesirable impurities contained in the feed or return/recycle streams. Such guard beds may be employed in the vapor or liquid streams. Suitable guard bed materials may include, for example, carbon, silica, alumina, ceramic, or resins. In one aspect, the guard bed media is functionalized, e.g., silver functionalized, to trap particular species such as sulfur or halogens.

The vapor-phase esterification reaction temperature is effected by the steady state composition and pressure, and typically may range from 50° C. to 200° C., e.g., from 80° C. to 190° C., from 125° C. to 175° C. The esterification process may be operated at atmospheric pressure but it is preferably operated at super-atmospheric pressure, e.g., from 105 to 700 kPa, from 110 to 350 kPa or from 120 to 300 kPa.

During the esterification process, an esterification product is withdrawn in vapor phase, preferably continuously, from reactor 103 via line 110. As shown in Table 1, the esterification product may comprise the following exemplary compositions.

TABLE 1

| ESTERIFICATION PRODUCT | | | |
|---|---|---|---|
| Component | Conc. (wt. %) | Conc. (wt. %) | Conc. (wt. %) |
| Ethyl Acetate | 10 to 90 | 25 to 85 | 25 to 70 |
| Acetic Acid | 10 to 90 | 15 to 70 | 20 to 60 |
| Water | 0.5 to 30 | 1 to 20 | 1 to 15 |
| Ethanol | 0.01 to 10 | 0.01 to 5 | 0.01 to 4 |
| Diethyl ether | <0.1 | <0.01 | <0.001 |
| Acetaldehyde | <2 | <1 | <0.5 |
| Diethyl acetal | <1 | <0.1 | <0.05 |
| n-butyl acetate | <1 | <0.5 | <0.02 |
| 2-butyl acetate | <2 | <1 | <0.75 |
| Iso-propyl acetate | <1 | <0.5 | <0.1 |

The amounts indicated as less than (<) in the tables throughout the present specification are preferably not present and if present may be present in trace amounts or in amounts greater than 0.0001 wt. %.

The trace impurities, such as n-butanol, 2-butanol, and/or iso-propanol, may be present in small amounts, if at all. Because these other alcohols may also be esterified, it is generally preferred to reduce the concentration of the other alcohols in the fed to the esterification unit.

In one embodiment, esterification product in line 110 is fed directly to a first column 104, also referred to as an "azeotrope column." In the embodiment shown in FIG. 2, line 110 is introduced in the lower part of first column 104. First column 104 may be a tray column having from 5 to 120 trays, e.g., from 15 to 80 trays or from 20 to 70 trays. In first column 104, acetic acid, a portion of the water, and other heavy components, if present, are withdrawn, preferably continuously, as first residue in line 113. First residue in line 113 may be reboiled as necessary to provide energy to drive the separation in column 104. First residue, or a portion thereof, in line 113 may be returned and/or recycled back to esterification zone 101 and fed to vaporizer 107. In addition, column 104 also recovers a first distillate in line 112. First distillate in line 112 may be condensed and further separated to recover an ester feed stream that is directed to hydrogenolysis zone 102 as described further herein.

In some embodiments, an optional vapor sidestream 111 from a lower portion of first column 104 which may be enriched in ethyl acetate as compared to first residue 113, may be withdrawn and returned to vaporizer 107. Optional vapor sidestream 111 may be withdrawn as a liquid or vapor and is preferably not reboiled in first column 104. Optional vapor sidestream 111 may provide energy necessary to drive vaporization in vaporizer 107 and thus reduce or eliminate the need for a reboiler.

The temperature of first column 104 at atmospheric pressure may vary. In one embodiment, the first residue exiting in line 113 preferably is at a temperature from 90° C. to 160° C., e.g., from 95° C. to 145° C. or from 100° C. to 140° C. The temperature of the first distillate exiting in line 112 preferably is from 60° C. to 125° C., e.g., from 85° C. to 110° C. or from 90° C. to 105° C. Column 104 may operate at an increased pressure, i.e., greater than atmospheric pressure. The pressure of column 104 may range from 105 to 510 kPa, from 110 to 475 kPa or from 120 to 375 kPa.

Exemplary components of the first distillate, and residue compositions for first column 104 are provided in Table 2 below. It should also be understood that the overhead stream and residue may also contain other components, not listed, such as components derived from the feed. For convenience, the residue of the first column may also be referred to as the "first residue." The distillates or residues of the other columns may be referred to with similar numeric modifiers (second, third, etc.) in order to distinguish them from one another, but such modifiers should not be construed as requiring any particular separation order.

TABLE 2

| FIRST COLUMN 104 | | | |
|---|---|---|---|
| | Conc. (wt. %) | Conc. (wt. %) | Conc. (wt. %) |
| First Distillate | | | |
| Ethyl Acetate | 50 to 99.5 | 60 to 95 | 75 to 90 |
| Water | 1 to 50 | 1 to 20 | 3 to 15 |
| Ethanol | 0.01 to 10 | 0.01 to 5 | 0.5 to 4 |
| Acetic Acid | <0.5 | <0.02 | <0.01 |

TABLE 2-continued

| FIRST COLUMN 104 | | | |
|---|---|---|---|
| | Conc. (wt. %) | Conc. (wt. %) | Conc. (wt. %) |
| First Residue | | | |
| Acetic Acid | 50 to 99.5 | 60 to 95 | 75 to 90 |
| Ethyl Acetate | 0.01 to 20 | 0.5 to 15 | 1 to 10 |
| Water | 0.01 to 15 | 0.5 to 12 | 1 to 10 |
| Ethanol | 0.001 to 5 | 0.001 to 3 | 0.01 to 2 |

3. Liquid Phase Esterification

Figure 3:
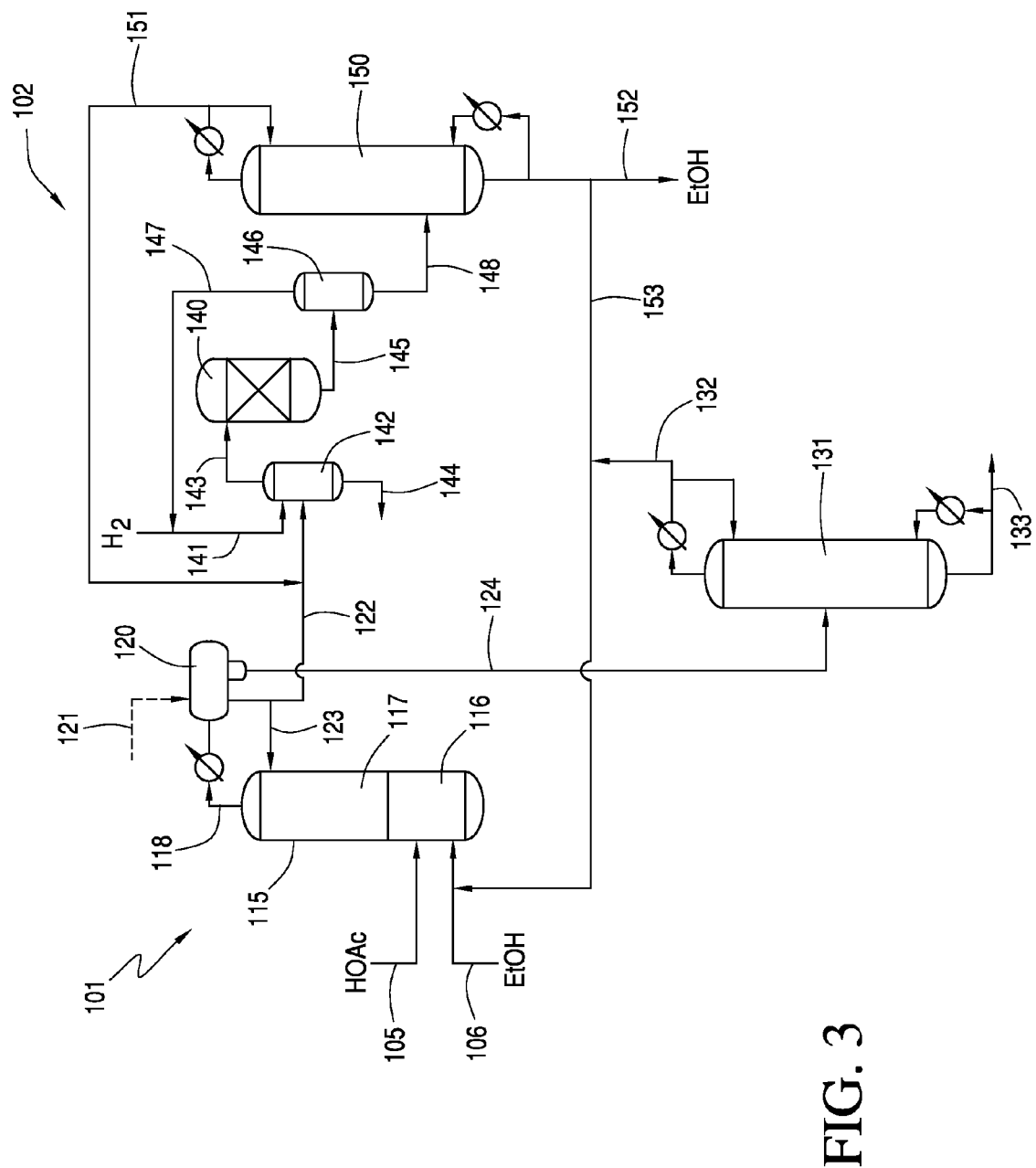
FIG. 3 is a schematic diagram of ethanol production process that directly feeds an organic phase of the esterification product produced by liquid esterification to the hydrogenolysis zone in accordance with one embodiment of the present invention.

In another embodiment, the esterification may be carried in the liquid phase in a distillation column 115 as shown in FIG. 3. The esterification can be operated under batch or continuous mode. For commercial purposes, continuous operation is preferred. Suitable liquid phase esterification reactions are further described in U.S. Pat. Nos. 6,768,021, 6,765,110, and 4,481,146, the entire contents and disclosures of which are hereby incorporated by reference. As shown in FIG. 3, ethyl acetate is typically produced by a series of steps employing a distillation column 115, also referred to as the first column in FIG. 3, and two feed streams, an acetic acid feed stream in line 105 and an ethanol feed stream in line 106. Both feed streams are continuously introduced, either separately or together, at the base of the distillation column 115, where the reaction zone 116 is located. In one embodiment, feed streams may be preheated prior to entering to the reaction zone 116, but it is preferred to maintain the feed streams in the liquid phase.

In FIG. 3, reaction zone 116 comprises a homogenous strongly acidic catalyst. Reaction zone 116 may comprise a suitable acidic catalyst such as methane sulfonic acid. When in solution, the acid catalyst is added to the reaction mixture so as to comprise from 0.1 to 10 wt. % of the reactor zone contents, e.g., from 0.01 to 5 wt. %. Optionally, the reaction zone contents may also contain 0.1 and 1 wt. % of a corrosion inhibitor. Suitable corrosion inhibitors include soluble copper inhibitors, such as copper ethanoate.

As indicated above, it may be preferred to maintain an excess molar amount of acetic acid in reaction zone 116. In general, the acetic acid concentration in the reaction zone 116 may range from 30 to 90 wt. %, e.g., from 50 to 80 wt. %, or from 60 and 70 wt. %. Optionally, a heavy ends stream may be purged from the bottom of the reaction zone 116.

In a continuous process, a corrosion resistant distillation column 115, constructed from a corrosion resistant material, such as stainless steel, may be used. Operation of homogeneous strong acid catalyzed esterification reactions in the base section of the distillation column 115 may requires the use of more corrosion resistant metallurgies. Higher temperatures further increase corrosion rates and, therefore, may require the use of even more corrosion resistant materials of construction. Feed flows continuously through reaction zone 116 and the esterification product simultaneously leaves the reaction zone 116 as a vapor and enters the distillation zone 117. Distillation zone 117 may comprise a series of 20 to 100 trays, e.g., from 30 to 80 trays or from 40 to 60 trays. The liquid-phase esterification reaction temperature is affected by the steady state composition and pressure, and the reaction zone 116 typically may range from 70° C. to 160° C., e.g., from 100° C. to 150° C., from 110° C. to 140° C. The esterification process may be operated at atmospheric pressure but it is preferable to operate reaction zone 116 at super-atmospheric pressure, e.g., from 101 to 300 kPa, from 110 to 250 kPa or from 120 to 200 kPa. One of skill in the art will recognize that various temperatures can be used depending on the pressure maintained in the reaction zone 116, and the specific ester being produced and the nature of reactants.

After reaction and distillation, the resulting vapors are removed from the top of the distillation column 115 as a first distillate in line 118. First distillate may comprise ethyl acetate, ethanol, water, and minor amounts of acetic acid. The amount of acetic acid in first distillate is preferably less than the amount of ethanol. The acetic acid concentration may be less than 600 wppm, e.g., less than 200 wppm or less than 50 wppm. Advantageously, low amounts of acetic acid in the first distillate may reduce the need to further remove acetic acid from the hydrogenolysis product.

Although esterification produces a mole of water for each mole of ethyl acetate, to control water in the esterification process a first distillate from distillation column 115 may contain a lower concentration of water than that formed by the esterification reaction.

Ethyl acetate/water may form an azeotrope having about 8.1 wt. % water and a boiling point around 70.4° C. at atmospheric pressure. In addition, ethyl acetate/ethanol/water may form an azeotrope having 8.4 wt. % ethanol and 9 wt. % water that has a boiling point around 70.2° C. at atmospheric pressure. For purposes of the present invention, the ethyl acetate/water azeotrope is primarily present in distillation zone 117 due to the relatively smaller ethanol concentrations in distillation zone 117.

In one embodiment, the water concentration in the first distillate is less than the azeotropic amount of water and ethyl acetate, e.g., less than about 10 wt. %, or less than about 9 wt. %. When the esterification reaction produces more water than the azeotropic amount, an azeotropic agent, such as ethyl acetate, may be added to distillation column 115. In one embodiment, about half of the water in the azeotrope of ethyl acetate and water is accounted for by the water from the esterification reaction. Adding liquid ethyl acetate with a lower water concentration may provide a net azeotroping capacity. In the production of pure ethyl acetate, a portion of the purified ethyl acetate may be fed to distillation column 115 to maintain a water concentration of less than about 10 wt. %. For purposes of the present invention, ethyl acetate recovered in the purification of the esterification product and/or ethyl acetate recovered in the purification of the hydrogenolysis product may be used as the azeotropic agent. In one embodiment, the azeotropic agent is a dry ethyl acetate composition that contains substantially no water.

The temperature of the first distillate exiting from column 115 preferably is from 60° C. to 125° C., e.g., from 70° C. to 115° C. or from 75° C. to 105° C. First distillate in line 118 may be condensed using refrigeration, cooling water, and/or an air cooled condenser, operating at a temperature of from 0° C. to 55° C., and further separated to recover an ester feed stream that is directed to hydrogenolysis zone 102 as described further herein.

4. Separation of Esterification Product

First distillate in line 112 from the vapor esterification in FIG. 2 or first distillate in line 118 from the liquid esterification in FIG. 3 may be biphasically separated in an overhead decanter 120. After esterification, the resulting vapors, e.g., esterification product, are collected at the top of the column as the first distillate and condensed. Condensing the first distillate may cause phase separation into a low density or lighter phase that is an organic phase rich in ethyl acetate and a more dense or heavier phase that is an aqueous phase rich in water. To further effectuate phasing, decanter 120 may be maintained a temperature from 0 to 40° C. In another embodiment, water may be added to decanter 120 to enhance phase separation via optional line 121. The optional water added to decanter 120 extracts ethanol from the organic phase thereby decreasing the water concentration in the organic phase. In other embodiments, the esterification product in the first distillate may have molar ratio of ethanol to ethyl acetate from 1:5 to 1:1.1, e.g., from 1:3 to 1:1.4, or from 1:2 to 1:1.25. A suitable molar ratio of ethanol to ethyl acetate to provide phasing may be 1.1:1.25. The low molar ratio of ethanol to ethyl acetate may also affect phasing. In addition, the low molar ratio of ethanol may also reduce the ethanol concentration in the organic phase and thus also reduce the water concentration in the organic phase.

Exemplary organic phase and aqueous phase compositions are provided in Table 3 below. These compositions may vary depending on the type of esterification reaction, e.g., liquid phase or vapor phase. Regardless of the type of esterification reaction, it is preferred that each phase contains very low concentrations of acetic acid, e.g., less than 600 wppm, e.g., less than 200 wppm or less than 50 wppm. In one embodiment, the organic phase comprises less than 6 wt. % ethanol and less than 5 wt. % water.

TABLE 3

| OVERHEAD DECANTER 120 | | | |
|---|---|---|---|
|  | Conc. (wt. %) | Conc. (wt. %) | Conc. (wt. %) |
| Organic Phase | | | |
| Ethyl Acetate | 60 to 99.5 | 60 to 97 | 75 to 95 |
| Water | 0.01 to 10 | 0.5 to 8 | 0.5 to 5 |
| Ethanol | 0.01 to 10 | 0.5 to 6 | 0.5 to 5 |
| Diethyl acetal | <1 | <0.1 | <0.05 |
| $C_3$+ alcohols | <1 | <0.1 | <0.05 |
| Aqueous Phase | | | |
| Water | 60 to 99.5 | 60 to 97 | 75 to 95 |
| Ethyl Acetate | 0.01 to 30 | 0.5 to 25 | 1 to 15 |
| Ethanol | 0.01 to 20 | 0.1 to 15 | 0.5 to 10 |
| Diethyl acetal | <0.1 | <0.01 | <0.001 |
| $C_3$+ alcohols | <1 | <0.1 | <0.05 |

In some embodiments, an organic phase comprising ethyl acetate is removed from decanter 120 via line 122. As shown in FIG. 2, a portion of the organic phase from decanter 120 may also be refluxed via line 123 to the upper portion of first column 104. Similarly, in FIG. 3, a portion of organic phase may be refluxed via line 123 to distillation column 115. In one embodiment, the reflux ratio is from 0.5:1 to 1.2:1, e.g., from 0.6:1 to 1.1:1 or from 0.7:1 to 1:1. The remaining portion of organic phase in line 122, or an aliquot portion thereof, may be directly fed as the ester feed stream to hydrogenolysis zone 102 as shown in FIGS. 2 and 3. In some embodiments, it may be preferred to preheat the organic phase directly fed to hydrogenolysis zone 102.

An aqueous phase comprising water is also removed from decanter 120 via line 124 and sent to recovery column 131, also referred to as the second column. Although a majority of the ethyl acetate is separated in the organic phase, a minor amount, e.g., less than 1%, or less than 0.75%, of the ethyl acetate in the decanter 120 may be withdrawn in the aqueous phase in line 124. In one embodiment, it is desirable to maximize ethyl acetate efficiency by recovering the ethyl acetate to be used as an azeotroping agent in first column 104 or to increase the ethyl acetate to ethanol in the hydrogenolysis zone 102. Optionally, a portion of the aqueous phase from the decanter 120 is purged and removed from the system.

Figure 4:
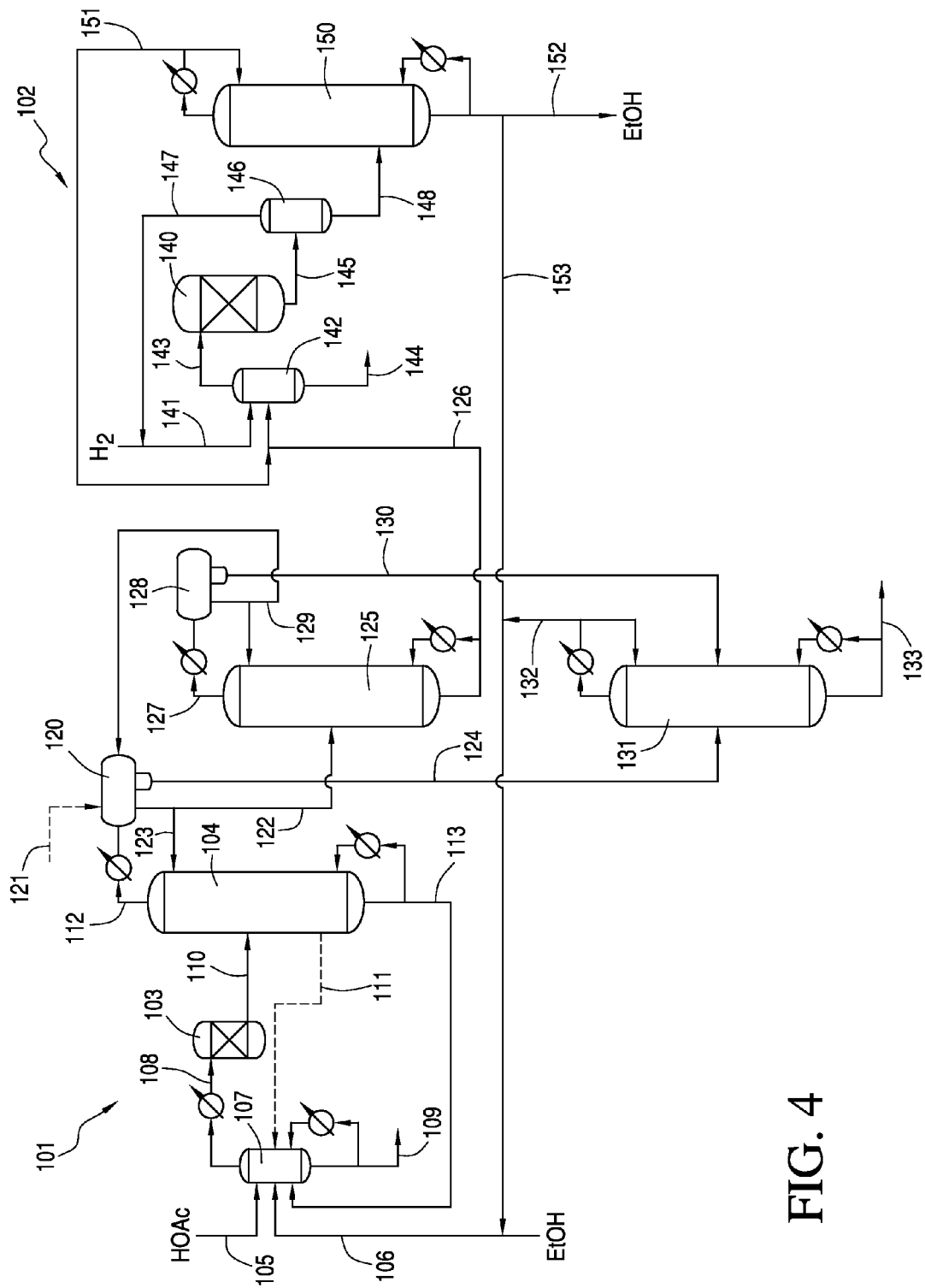
FIG. 4 is a schematic diagram of ethanol production process that uses a purification column to remove water and/or ethanol from the organic phase in accordance with one embodiment of the present invention.
Figure 5:
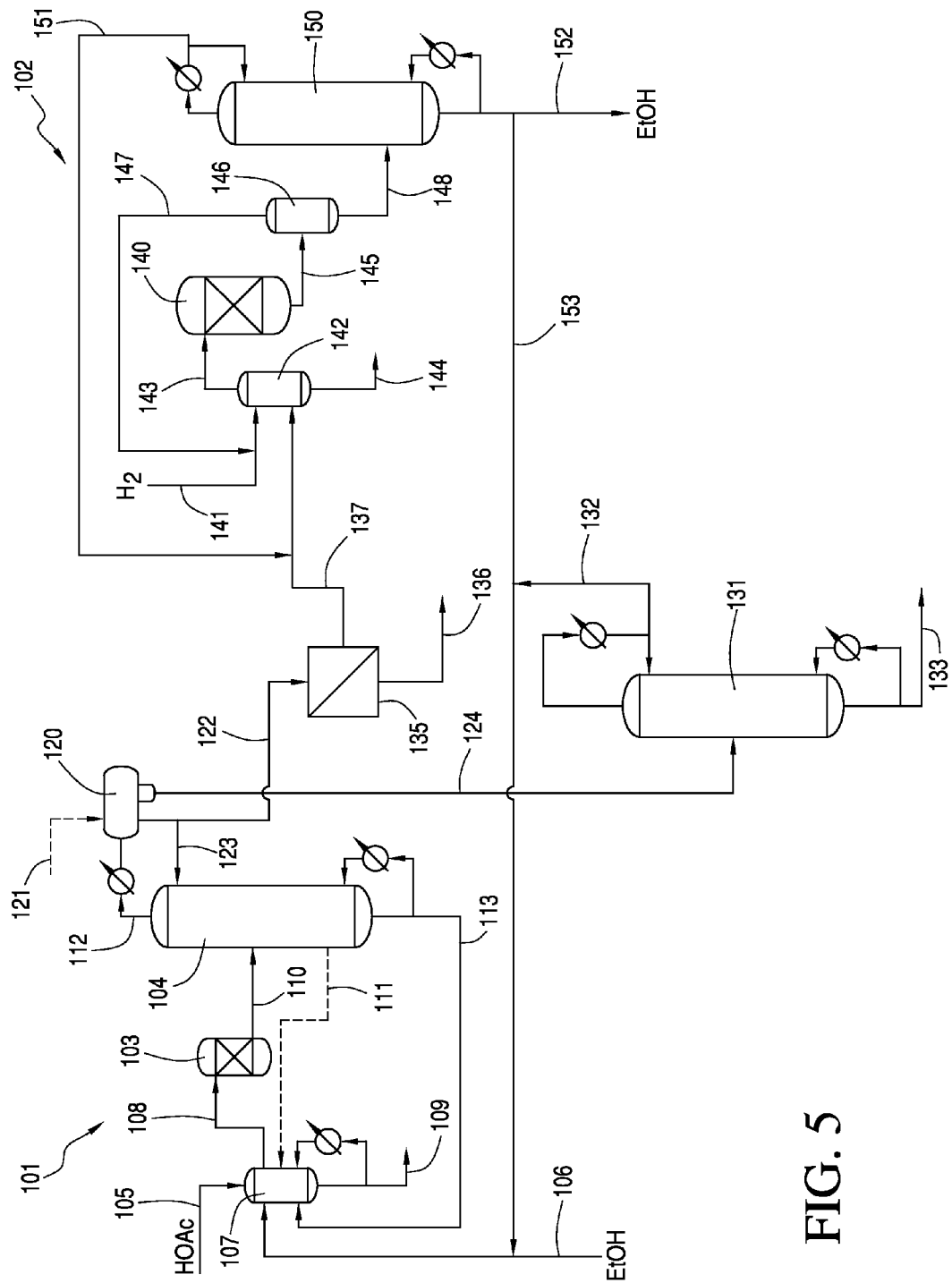
FIG. 5 is a schematic diagram of ethanol production process that uses a membrane unit to remove water from the organic phase in accordance with one embodiment of the present invention.

In some embodiments, it may be desirable to further process the organic phase prior to entering hydrogenolysis zone 102. This may allow feeding a non-aliquot portion of the organic phase to the hydrogenolysis zone 102. As shown in FIG. 4, the organic phase may be fed to a purification column 125 to reduce the ethanol and/or water concentrations and remove impurities. In another embodiment, the organic phase may be fed to a membrane separation unit or pervaporization ("pervap") unit 135 to reduce water concentrations as shown in FIG. 5. In further embodiments of the present invention, the organic phase may be fed to a pervap unit 135 and purification column in series. Although FIGS. 4 to 10 are shown with a vapor esterification reactor similar to FIG. 2, in other embodiments of the present invention, a liquid esterification reaction similar to FIG. 3 may be used with the embodiments shown in FIGS. 4 to 10.

a. Purification Column

Purification column 125 removes ethanol and water from ethyl acetate in the organic phase. In particular, column 125 may purify ethyl acetate in the organic phase by removing one or more azeotropes of ethyl acetate. Depending on the composition of organic phase and the phasing in decanter 120, a purification column 125 may be advantageous when the ethanol and/or water concentration in the organic phase exceeds 5 wt. %, e.g., exceeds 8 wt. % or exceeds 10 wt. %. Any water fed to hydrogenolysis zone 102 would be expected to pass through and would need to be removed from the final ethanol if desired. Additional ethanol fed to hydrogenolysis reactor 140 may have less of an impact, but may create capacity restrains and bottlenecking.

Purification column 125 may be a tray or packed column. In one embodiment, purification column 125 is a tray column having from 10 to 80 trays, e.g., from 20 to 60 trays or from 30 to 50 trays. Although the temperature and pressure of purification column 125 may vary, when at 65 kPa the temperature of the overhead preferably is from 70° C. to 100° C., e.g., from 75° C. to 95° C. or from 80° C. to 90° C. The temperature at the base of the purification column 125 preferably is from 80° C. to 110° C., e.g., from 85° C. to 105° C. or from 90° C. to 100° C. In other embodiments, the pressure of purification column 125 may be from 10 kPa to 600 kPa, e.g., from 20 kPa to 400 kPa or from 20 kPa to 300 kPa.

Ethyl acetate is preferably removed as a residue stream, i.e. ester-enriched stream, in line 126 and a portion thereof may be fed to a reboiler. In some embodiments, ethyl acetate may be removed as a sidestream (not shown) from the base of column 125 and a residue may be removed and purged. Residue stream in line 126 preferably has a low concentration of ethanol and/or water, which may be less than 2 wt. % individually or collectively, e.g., less than 1 wt. % or less than 0.1 wt. %. The residue stream in line 126 may be directly fed as the ester feed stream to hydrogenolysis zone 102. In one embodiment, residue stream in line 126 has a higher temperature than the organic phase 122, and thus it may be advantageous to directly feed residue stream in line 126 to hydrogenolysis zone 102 because no further preheating is required. In one exemplary embodiment, residue stream in line 126 may have a temperature that is at least 70° C., e.g., at least 80° C. or 85° C. Advantageously, removing impurities in organic phase may efficiently use energy in the system and reduce capital expenses for additional utility heaters.

The distillate of the purification column 125 is an ethyl-acetate-ethanol-water stream and is preferably condensed in line 127 by passing through subcooler before being fed to a decanter 128, in which an organic phase is separated from an aqueous phase. A portion or all of the organic phase in line 129, which comprises ethyl acetate and/or ethanol, may be refluxed to the top of purification column 125. In one embodiment, the reflux ratio is from 0.25:1 to 1:0.25, e.g., from 0.5:1 to 1:0.5 or from 1:1 to 1:2. All or a portion of remaining organic phase in line 129 may also be returned to vaporizer 107, first column 104, and/or overhead decanter 120 as shown in FIG. 4.

In some optional embodiments, not shown, ethyl acetate may be removed as a sidestream near the base of purification column 125. When ethyl acetate is removed as a side stream, the bottoms stream from purification column 125 is preferably withdrawn and may be recycled to vaporizer 107 or first column 104 as an azeotroping agent. The optional bottoms stream comprising ethyl acetate acts as an azeotroping agent to assist in the removal of water produced in reactor 103. In one embodiment, a conductivity meter may be used to monitor the acetic acid concentration in the organic phase. When the concentration of acetic acid is greater than a tolerable level for the hydrogenolysis reactor, a purification column 125 may be used to remove acetic acid in the optional bottom stream.

The aqueous phase may be withdrawn from decanter 128 via line 130 and preferably is fed to recovery column 131. The aqueous phases in lines 124 and/or 130 may be co-fed to recovery column 131 or separately fed to recovery column 131. In one embodiment a portion of the aqueous phase of decanter 128 in line 130 is purged and removed from the system.

b. Recovery Column

Recovery column 131 is operated to remove a significant portion of any organic content in aqueous phase in line 124 prior to purging the water. Recovery column 131 may also remove organics from the aqueous phase in line 130 form the purification column 125. Recovery column 131 may be a tray or packed column. In one embodiment, recovery column 131 is a tray column having from 10 to 80 trays, e.g., from 20 to 75 trays or from 30 to 60 trays. Although the temperature and pressure of recovery column 131 may vary, when at atmospheric pressure the temperature of the overhead preferably is from 60° C. to 85° C., e.g., from 65° C. to 80° C. or from 70° C. to 75° C. The temperature at the base of recovery column 131 preferably is from 92° C. to 118° C., e.g., from 97° C. to 113° C. or from 100° C. to 108° C. In other embodiments, the pressure of recovery column 131 may be from 1 kPa to 300 kPa, e.g., from 10 kPa to 200 kPa or from 10 kPa to 150 kPa.

In one embodiment, any of the feeds to recovery column 131 may be at the top of the tower, i.e. near or into the reflux line. This keeps a sufficient loading on the trays such that the column operates as a stripping tower.

Exemplary second distillate and second residue compositions of recovery column 131 are provided in Table 4 below.

TABLE 4

RECOVERY COLUMN 131

| | Conc. (wt. %) | Conc. (wt. %) | Conc. (wt. %) |
|---|---|---|---|
| Second Distillate | | | |
| Ethyl Acetate | 20 to 80 | 35 to 75 | 40 to 55 |
| Water | 5 to 50 | 10 to 40 | 10 to 35 |
| Ethanol | 5 to 50 | 10 to 40 | 10 to 35 |
| $C_3$+ Acetates | <1 | <0.1 | <0.01 |
| $C_3$+ alcohols/ketones | <1 | <0.5 | <0.2 |
| Second Residue | | | |
| Water | 85 to 99.9 | 90 to 99.9 | 97 to 99.9 |
| Ethyl Acetate | 0.001 to 15 | 0.001 to 5 | 0.01 to 2 |
| Ethanol | 0.001 to 15 | 0.001 to 5 | 0.01 to 2 |
| $C_3$+ Acetates | <1 | <0.1 | <0.01 |
| $C_3$+ alcohols/ketones | <1 | <0.05 | <0.01 |

The second distillate of recovery column 131 in line 132 may be condensed and refluxed, as necessary, to the top of recovery column 131. Depending on the composition of overhead in line 132, the overhead may be returned to the vaporizer 107, first column 104, or co-fed with a portion of the organic phase in line 122 to the hydrogenolysis zone 102. When the second distillate in line 132 is fed to the hydrogenolysis zone 102, it is preferable to control the total concentration of water such that it is less than 8 wt. % based on the total feed to the hydrogenolysis section, e.g., less than 5 wt. % or less than 3 wt. %. In addition, particularly when the stream is relatively small, a portion of the second distillate in line 132 may be purged.

The second residue of recovery column 131, which mainly comprises water, is withdrawn in line 133. The water in line 133 may be purged from the system and optionally sent to waste water treatment. In some embodiments, a portion of the water may be returned to the decanter 120 and/or decanter 128 to maintain a desired water concentration for separation, fed as an extractive agent to one or more columns in the system, or used to hydrolyze impurities such as diethyl acetal in the process.

c. Membrane

In some embodiments as shown in FIG. 5, it may be desirable to further process the organic phase to remove water prior to being directed to hydrogenolysis zone 102. A portion of the organic phase in line 122 may pass to a membrane separation unit, or a pervap unit 135. The membrane separation unit or pervap unit may be employed to primarily permeate the water present in the organic phase. This creates a dried organic phase retentate that may be fed as an ester feed stream to hydrogenolysis zone 102. Membrane separation or pervap units are well known to those skilled in the art and are available from, among others, Sulzer Chemtech GmbH and Artisan Industries, Inc.

Suitable membranes include shell and tube membrane modules having one or more porous material elements therein. Non-porous material elements may also be included. The material elements may include a polymeric element such as polyvinyl alcohol, cellulose esters, and perfluoropolymers. Membranes that may be employed in embodiments of the present invention include those described in Baker, et al., "Membrane separation systems: recent developments and future directions," (1991) pages 151-169, Perry et al., "Perry's Chemical Engineer's Handbook," 7th ed. (1997), pages 22-37 to 22-69, the entireties of which are incorporated herein by reference.

In other embodiments, water separation may be facilitated using an adsorption unit, molecular sieves, azeotropic distillation column, or a combination thereof.

Using a membrane separation unit 135 to remove water may provide an advantage over other means of removing water. Preferably at least 60% of the water in the organic phase in line 122 is removed, e.g., at least 75% or at least 90%. The resulting dried organic phase in line 137 preferably comprises less than 2 wt. % water, e.g., less than 1 wt. % water or less than 0.5 wt. % water, and may be either processed further in a purification column 125 as described above in FIG. 4 or directly fed as an ester feed stream to hydrogenolysis zone 102 as shown in FIG. 5. In addition, a portion of the dried organic phase in line 137 may be fed to first column 104 as an azeotrope agent. In some embodiments, the pervap unit 135 may also remove additional alcohol from the organic phase. The permeate stream in line 136 preferably comprises water and may be purged from the system, returned to the decanter 120 or fed to recovery column 131. When purging permeate water in line 136, it may be combined with bottom in line 133.

In some embodiments, organic phase in line 123 may not be refluxed to first column 104. Instead, a portion of the dried organic phase in line 137 may be refluxed. This allows a dried reflux which advantageously reduces the water in the overhead of first column 104 and may allow for less azeotroping agent to be used in first column 104. Reducing the amount of azeotroping agent allows for more of the ethyl acetate produced to be converted to ethanol and increases ethanol production. In other embodiments, membrane separation unit 135 may be used after extractive column 170 to remove water from the ester stream feed in line 175.

d. Extractive Column

Figure 6:
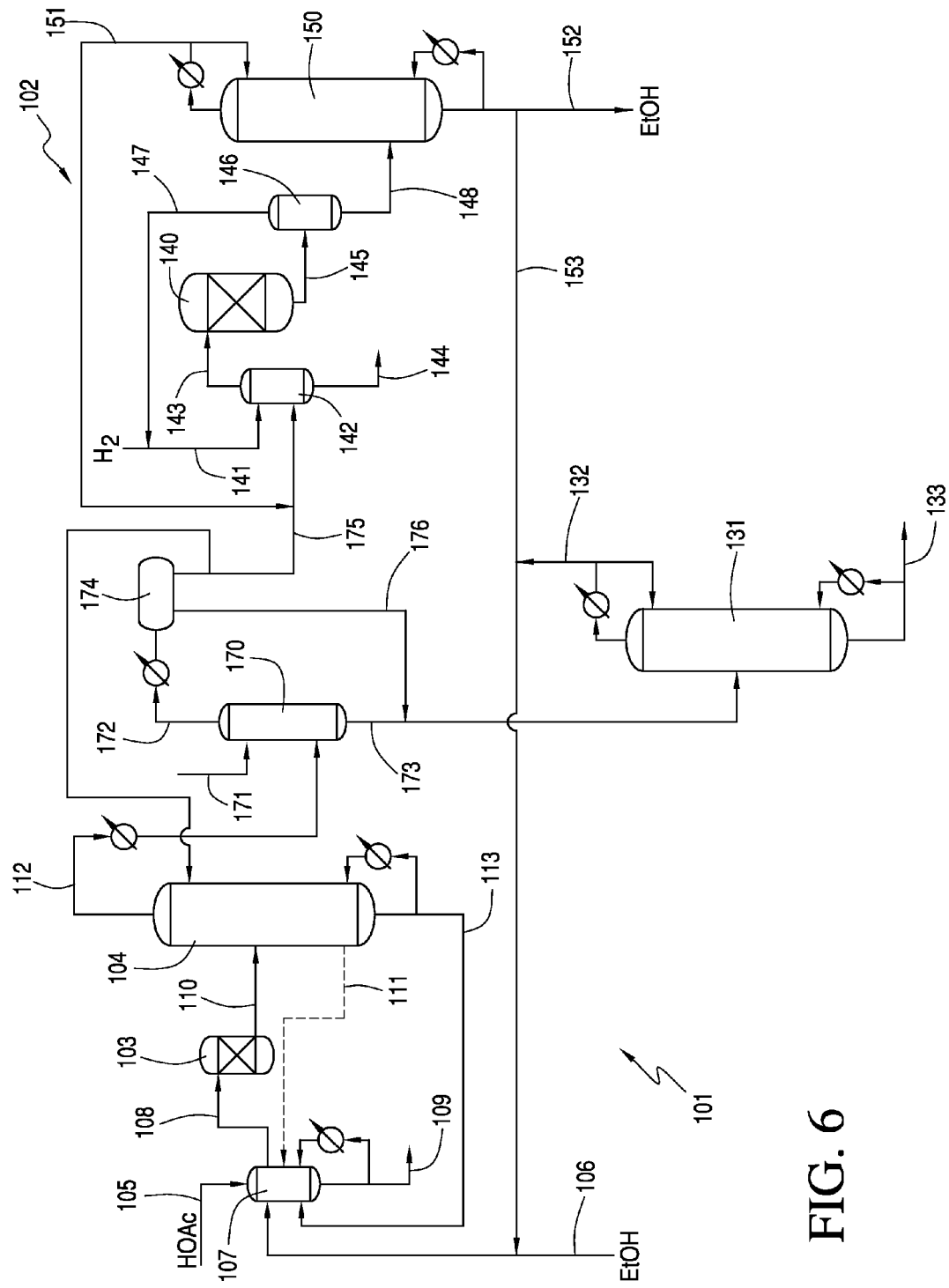
FIG. 6 is a schematic diagram of ethanol production process that uses an extractive column to prepare an ester feed stream for the hydrogenolysis unit in accordance with one embodiment of the present invention.

In another embodiment, an ester feed stream may be recovered from the first distillate in line 112 using an extractive column 170 as shown in FIG. 6. Extractive column 170 may have one or more trays. Multi-stage extraction may also be used. In one aspect, an extractive column 170 may be used when the ethanol concentration in the esterification product is large. This may be a result of an incomplete conversion in reactor 103 or excess ethanol fed to reactor 103. Optionally, extractive column 170 may be used in combination with an overhead decanter on first column 104 and the organic phase may be fed to extractive column 170.

As shown in FIG. 6 first distillate in line 112 may be condensed and fed to a lower portion of extractive column 170. When extractive column 170 is used, it is not necessary to reflux the condensed first distillate because doing so will introduce water to first column 104. In addition to first distillate, an extractive agent in line 171 is fed at a point above the feedpoint of first distillate. In one embodiment, extractive agent is fed at a point to allow extractant to be present on a majority of the stages within extractive column 170. The extractive agent preferably comprises water. The feed ratio of extractive agent to first distillate may be from 5:1 to 1:5, e.g., from 3:1 to 1:3 or 2:1 to 1:2. Extractive column 170 recovers an extractant in line 172 that comprises ethyl acetate and contains less than 5 wt. % water, e.g., less than 4 wt. % water or less than 3 wt. % water. The raffinate in line 173 may comprise water and ethanol may be fed to recovery column 131. A portion of the bottoms from recovery column 131 may be returned to the extractive column 170 as the extractive agent.

The extractant in line 172 may be separated, preferably biphasically separated, in a hold up tank 174. Although extractant in line 172 may have very low water concentration, e.g., less than first distillate, some water may be present. Hold up tank 174 provides sufficient residence time to allow an organic phase in line 175, rich ethyl acetate, to be separated from extractant in line 172. Organic phase in line 175 comprises low concentrations of water, e.g., of less than 3 wt. %. Optionally an overhead decanter may be used. Organic phase in line 175, due to the relative lower water concentration than first distillate, may be refluxed to first column 104. The reflux ratio may vary but preferably is less than 5:1, e.g., less than 3:1 or less than 2:1. A portion of organic phase in line 175, or an aliquot portion thereof, may be directly fed as the ester feed stream to hydrogenolysis zone 102 as shown. In some embodiments, it may be preferred to preheat the organic phase directly fed to hydrogenolysis zone 102. An aqueous phase comprising water is also removed from hold up tank 174 via line 176 and combined with raffinate in line 173.

Although the temperature and pressure of extractive column 170 may vary, the temperature of the extracted overhead preferably is from 20° C. to 60° C., e.g., from 25° C. to 55° C. or from 30° C. to 50° C. The temperature at the base of the extractive column 170 preferably is from 20° C. to 60° C., e.g., from 25° C. to 55° C. or from 30° C. to 50° C. In other embodiments, the pressure of extractive column 170 may be from 80 kPa to 400 kPa, e.g., from 90 kPa to 300 kPa or from 100 kPa to 200 kPa.

Optionally the first distillate in line 112 may be biphasically separated and the organic phase thereof may be refluxed to column 104. In these optional embodiments, it may not be necessary to reflux any of the organic phase of the extractant.

In some embodiments, the organic phase may be further purified using purification column and/or membrane as described above before being fed to hydrogenolysis zone 102.

III. Hydrogenolysis

In general, the ethyl acetate produced by the esterification reaction zone 101 is fed as the ester feed stream to the hydrogenolysis reaction zone 102. As described above, ethyl acetate may be further purified from the esterification product before being fed to hydrogenolysis reaction zone 102. Regardless of the purification method, the ester feed stream preferably comprises less than 5 wppm esterification catalyst, e.g., less than 1 wppm, or less than 0.1 wppm. In addition, although acetic acid may not be separated from the esterification product, the process preferably is controlled such that the ester feed stream comprises less than 1 wt. % acetic acid, e.g., less than 0.1 wt. %, or less than 0.01 wt. %.

The amount of ethanol and/or water, if any, in the ester feed stream depends on the purification of the ester feed stream as described above. Preferably, the ester feed stream comprises less than 6 wt. % ethanol, e.g., less than 5 wt. % or less than 2 wt. %. The ester feed stream may also comprises less than 8 wt. % water, e.g., less than 5 wt. % or less than 2 wt. %.

A. Hydrogenolysis Reaction

As shown in FIG. 2, the organic phase in line 122 is referred to as the ester feed stream. In one embodiment, the ester feed stream 122 and hydrogen via feed line 141 are separately introduced into a vaporizer 142 to create a vapor feed stream in line 143 that is directed to hydrogenolysis reactor 140. In one embodiment, lines 122 and 141 may be combined and jointly fed to vaporizer 142. A vapor feed stream in line 143 is withdrawn from vaporizer 142 and is preheated by passing through a heat exchanger. The temperature of the vapor feed stream in line 143 after passing through the heat exchanger is preferably from 100° C. to 350° C., e.g., from 200° C. to 325° C. or from 250° C. to 300° C. Vaporizer 142 preferably operates at a pressure from 700 to 8,500 kPa, e.g., from 1,500 to 7,000 kPa, or from 2,000 to 6,500 kPa. Any feed that is not vaporized is removed from vaporizer 142 as a blowdown stream 144. Blowdown stream 144 may be discarded from the hydrogenolysis zone 102.

Although vapor feed stream in line 143 is shown as being directed to the top of hydrogenolysis reactor 140, line 143 may be directed to the side, upper portion, or bottom of hydrogenolysis reactor 140.

Hydrogen fed to hydrogenolysis reactor 140 may be obtained from syngas. In addition, hydrogen may also originate from a variety of other chemical processes, including ethylene crackers, styrene manufacturing, and catalytic reforming. Commercial processes for purposeful generation of hydrogen include autothermal reforming, steam reforming and partial oxidation of feedstocks such as natural gas, coal, coke, deasphalter bottoms, refinery residues and biomass. Hydrogen may also be produced by electrolysis of water. In one embodiment, the hydrogen is substantially pure and contains less than 10 mol. % carbon monoxide and/or carbon dioxide, e.g., less than 5 mol. % or less than 2 mol. %.

In one embodiment, the molar ratio of hydrogen to ethyl acetate that is introduced into hydrogenolysis reactor 140 is greater than 2:1, e.g. greater than 4:1, or greater than 12:1. In terms of ranges the molar ratio may be from 2:1 to 100:1, e.g., 4:1 to 50:1, or from 12:1 to 20:1. Without being bound by theory higher molar ratios of hydrogen to ethyl acetate, preferably from 8:1 to 20:1, are believed to result in high conversion and/or selectivity to ethanol.

Hydrogenolysis reactor 140 may comprise any suitable type of reactor, such as a fixed bed reactor or a fluidized bed reactor. Hydrogenolysis reactions are exothermic and in many embodiments, an adiabatic reactor may be used for the hydrogenolysis reactor. Adiabatic reactors have is little or no need for internal plumbing through the reaction zone to add or remove heat. In other embodiments, a radial flow reactor or reactors may be employed, or a series of reactors may be employed with or without heat exchange, quenching, or introduction of additional feed material. Alternatively, a shell and tube reactor provided with a heat transfer medium may be used.

In preferred embodiments, a catalyst is employed in a fixed bed reactor, e.g., in the shape of a pipe or tube, where the reactants, typically in vapor form, are passed over or through the catalyst. Other reactors, such as fluid or ebullient bed reactors, can be employed. In some instances, a hydrogenolysis catalyst may be used in conjunction with an inert material to regulate the pressure drop of the reactant stream through the catalyst bed and the contact time of the reactant compounds with the catalyst particles.

The hydrogenolysis process may be operated in a vapor phase, or a mixed vapor/liquid phase regime. The mixed vapor/liquid phase regime is where the reactant mixture in line 143, at the reactor conditions, is below the dew point temperature. The hydrogenolysis reaction may change from a mixed vapor/liquid phase to a fully vapor phase reaction, as the reaction proceeds down the reactor. The mixed phase hydrogenolysis may also be conducted in other types of reactors, or within a combination of different reactors, for example in a slurry or stirred tank reactor with, or without, external circulation and optionally operated as a cascade or stirred tank, a loop reactor or a Sulzer mixer-reactor. The hydrogenolysis process may be conducted in batch, semi-continuous, or continuous mode. For industrial purposes, continuous mode of operation is the most efficient.

In some embodiments, the hydrogenolysis reactor may comprise other types of reactors, such as fluidized bed, spinning basket and buss loop, or heat exchanger reactors. A mixed vapor/liquid phase hydrogenolysis reaction can be conducted with co-flow or counterflow of the vapor, e.g., hydrogen, to the liquid, i.e. ester feed stream, in a bubble reactor. Trickle bed reactors may also be used.

In one embodiment, a heterogeneous catalyst is used in hydrogenolysis reactor 140. The catalyst may be a copper-based catalyst. Copper-based catalyst may comprise copper chromite, copper and zinc, and/or copper-zinc-oxide. Other copper-based catalyst may include an $MgO$—$SiO_2$ support that is impregnated with copper. Mixed copper oxide based catalyst may include copper and a second metal selected from zinc, zirconium, manganese, and/or oxides thereof. In some embodiments, aluminum oxide may also be present in the catalyst. The presence of aluminum oxide is believed to increase the heavy alcohol, and/or ketone concentrations during the reduction of ethyl acetate due to the presence of acidic sites. In those embodiments, the catalyst may comprise a basic component, such as magnesium or calcium, to reduce the acidic sites or the aluminum oxide concentration may be very low, e.g., less than 0.1 wt. %. In some embodiments, the catalyst may be substantially free of aluminum oxide.

A suitable copper-based catalyst may comprises from 30 to 70 wt. % copper oxide, 15 to 45 wt. % zinc oxide, and/or 0.1 to 20 wt. % aluminum oxide. More preferably, a copper-based catalyst may comprises from 55 to 65 wt. % copper oxide, 25 to 35 wt. % zinc oxide, and/or 5 to 15 wt. % aluminum oxide. Preferably, the copper-based catalyst is supported on zinc oxide and preferably comprises from 20 to 40 wt. % of copper, in terms of the metal content.

In other embodiments, the catalyst employed in hydrogenolysis reactor 140 may be a Group VIII-based catalyst. Group VIII-based catalyst may comprise a Group VIII metal selected from the group consisting of iron, ruthenium, osmium, cobalt, rhodium, iridium, nickel, palladium, and platinum. In addition, there may be one or more secondary promoter metals selected from the group consisting of zinc, cobalt, tin, germanium, lead, rhenium, tungsten, molybdenum. Group VIII-based catalysts may advantageously be supported on any suitable support known to those skilled in the art; non-limiting examples of such supports include carbon, silica, titania, clays, aluminas, zinc oxide, zirconia and mixed oxides. Preferably, the palladium based catalyst is supported on carbon. In addition, the Group VIII-based catalyst may be supported on any suitable support, such as silica, silica-alumina, calcium metasiciliate, carbon, titania, clays, aluminas, zinc oxide, zirconia, and mixed metal oxides. For example, palladium based catalysts may be supported on carbon.

The reduction of ethyl acetate to produce ethanol, e.g., in the hydrogenolysis reactor 140, is typically conducted at elevated temperatures from 125° C. to 350° C., e.g., from 180° C. to 345° C., from 225° C. to 310° C., or from 290° C. to 305° C. Reaction temperatures greater than 240° C., or greater than 260° C., may increase conversion of ethyl acetate. Although not bound by theory, it is believed that reduced temperatures in the hydrogenolysis reactor of less than 275° C. may suppress the formation of heavy impurities such as alcohols and/or ketones. The pressure in the hydrogenolysis reactor may operate under high pressure from of greater than 1000 kPa, e.g., greater than 3,000 kPa or greater than 5,000 kPa. In terms of ranges the pressure in the hydrogenolysis reaction may be from 700 to 8,500 kPa, e.g., from 1,500 to 7,000 kPa, or from 2,000 to 6,500 kPa. Pressure greater than 2,500 kPa may be more favorable for improving ethanol productivity and/or selectivity. The reactants may be fed to hydrogenolysis reactor at a gas hourly space velocity (GHSV) of greater than 500 hr$^{-1}$, e.g., greater than 1000 hr$^{-1}$, greater than 2500 hr$^{-1}$ or even greater than 5000 hr$^{-1}$. In terms of ranges the GHSV may range from 50 hr$^{-1}$ to 20,000 hr$^{-1}$, e.g., from 1000 hr$^{-1}$ to 10,000 hr$^{-1}$, or from 2000 hr$^{-1}$ to 7,000 hr$^{-1}$.

In particular, the reaction of ethyl acetate may achieve favorable conversion of ethyl acetate and favorable selectivity and productivity to ethanol. For purposes of the present invention, the term "conversion" refers to the amount of ethyl acetate in the feed that is converted to a compound other than ethyl acetate. Conversion is expressed as a mole percentage based on ethyl acetate in the feed. The conversion may be at least 50%, e.g., at least 70%, at least 90%. In terms of ranges, the conversion of ethyl acetate may range from 50 to 98%, e.g., from 60 to 95% or from 70 to 90%. Although catalysts and reaction conditions that have high conversions may be possible, such as greater than 90% or greater than 95%, in some embodiments a low conversion may be acceptable at high selectivity for ethanol. Compensating for low conversion by appropriate recycle streams or use of larger reactors may be easier than compensating for poor selectivity to ethanol.

Selectivity is expressed as a mole percent based on converted ethyl acetate. It should be understood that each compound converted from ethyl acetate has an independent selectivity and that selectivity is independent from conversion. For example, if 90 mole % of the converted ethyl acetate is converted to ethanol, we refer to the ethanol selectivity as 90%. The selectivity to ethanol is preferably at least 80%, e.g., at least 90% or at least 95%.

The term "productivity," as used herein, refers to the grams of a specified product, e.g., ethanol, formed during the hydrogenolysis, based on the kilograms of catalyst used per hour. A productivity of at least 100 grams of ethanol per kilogram of catalyst per hour, e.g., at least 500 grams of ethanol per kilogram of catalyst per hour or at least 1,000 grams of ethanol per kilogram of catalyst per hour, is preferred. In terms of ranges, the productivity preferably is from 100 to 3,000 grams of ethanol per kilogram of catalyst per hour, e.g., from 400 to 2,500 grams of ethanol per kilogram of catalyst per hour or from 600 to 2,000 grams of ethanol per kilogram of catalyst per hour.

A crude reaction mixture is preferably withdrawn continuously from hydrogenolysis reactor 140 via line 145. Any water in ester feed stream may pass through the hydrogenolysis reactor and be present in a similar amount in the crude reaction mixture. The composition of the crude reaction mixture may vary depending on the ester feed stream, conversion, and selectivity. Exemplary crude reaction mixtures, excluding hydrogen and other gases such as methane, ethane, carbon monoxide and/or carbon dioxide, are shown in Table 5 below.

TABLE 5

CRUDE REACTION MIXTURE

| Component | Conc. (wt. %) | Conc. (wt. %) | Conc. (wt. %) |
|---|---|---|---|
| Ethanol | 35 to 95 | 40 to 85 | 50 to 80 |
| Ethyl Acetate | 0.5 to 40 | 1 to 30 | 1 to 25 |
| Water | 0.001 to 10 | 0.001 to 5 | 0.001 to 3 |
| Aldehyde | <2 | 0.001 to 1.5 | 0.01 to 1 |
| Acetic Acid | <0.5 | <0.01 | <0.001 |
| Diethyl acetal | <1 | <0.1 | <0.05 |
| n-butanol | <1 | <0.5 | <0.1 |
| 2-butanol | 0.01 to 2 | 0.05 to 1.5 | 0.1 to 1 |
| Iso-propanol | <1 | <0.1 | <0.05 |
| Acetone | <1 | <0.5 | <0.1 |
| Heavies | <1 | <0.5 | <0.1 |
| Carbon Gases | 0.1 to 10 | 0.01 to 5 | 0.01 to 3 |

Heavies in Table 5 include organic compounds that have a larger molecular weight than ethanol, such as n-butyl acetate, sec-butyl acetate, ethyl butyrate, isopropyl acetate, 2-methyl-1-propanol, etc. Other acetates, aldehydes, and/or ketones may also be encompassed by heavies. The carbon gases refers to any carbon containing compound that is a gas at standard temperature and pressure, such as carbon monoxide, carbon dioxide, methane, ethane, etc. In one embodiment, the hydrogenolysis reaction is controlled to maintain low impurity concentrations of acetone, n-butanol, and 2-butanol.

B. Separation

The crude reaction mixture in line 145 may be condensed and fed to a separator 146, which, in turn, provides a vapor stream 147 and a liquid stream 148. In some embodiments, separator 146 may comprise a flasher or a knockout pot. Although one separator 146 is shown, there may be multiple separators in some embodiments of the present invention. The separator 146 may operate at a temperature of from 20° C. to 250° C., e.g., from 30° C. to 225° C. or from 60° C. to 200° C. The pressure of separator 146 may be from 50 kPa to 2000 kPa, e.g., from 75 kPa to 1500 kPa or from 100 kPa to 1000 kPa.

Vapor stream 147 exiting separator 146 may comprise hydrogen, carbon monoxide, carbon dioxide, and hydrocarbons, and may be purged and/or returned to hydrogenolysis reactor 140. In some embodiments, the returned vapor stream 147 may be compressed before being combined with hydrogen feed 141. Vapor stream 147 may comprise inert gases, such as nitrogen, or nitrogen may be fed to vapor stream 147 to increase molecular weight for improved polytropic compression requirements. Vapor stream 147 may be combined with the hydrogen feed 141 and co-fed to vaporizer 142.

Figure 8A:
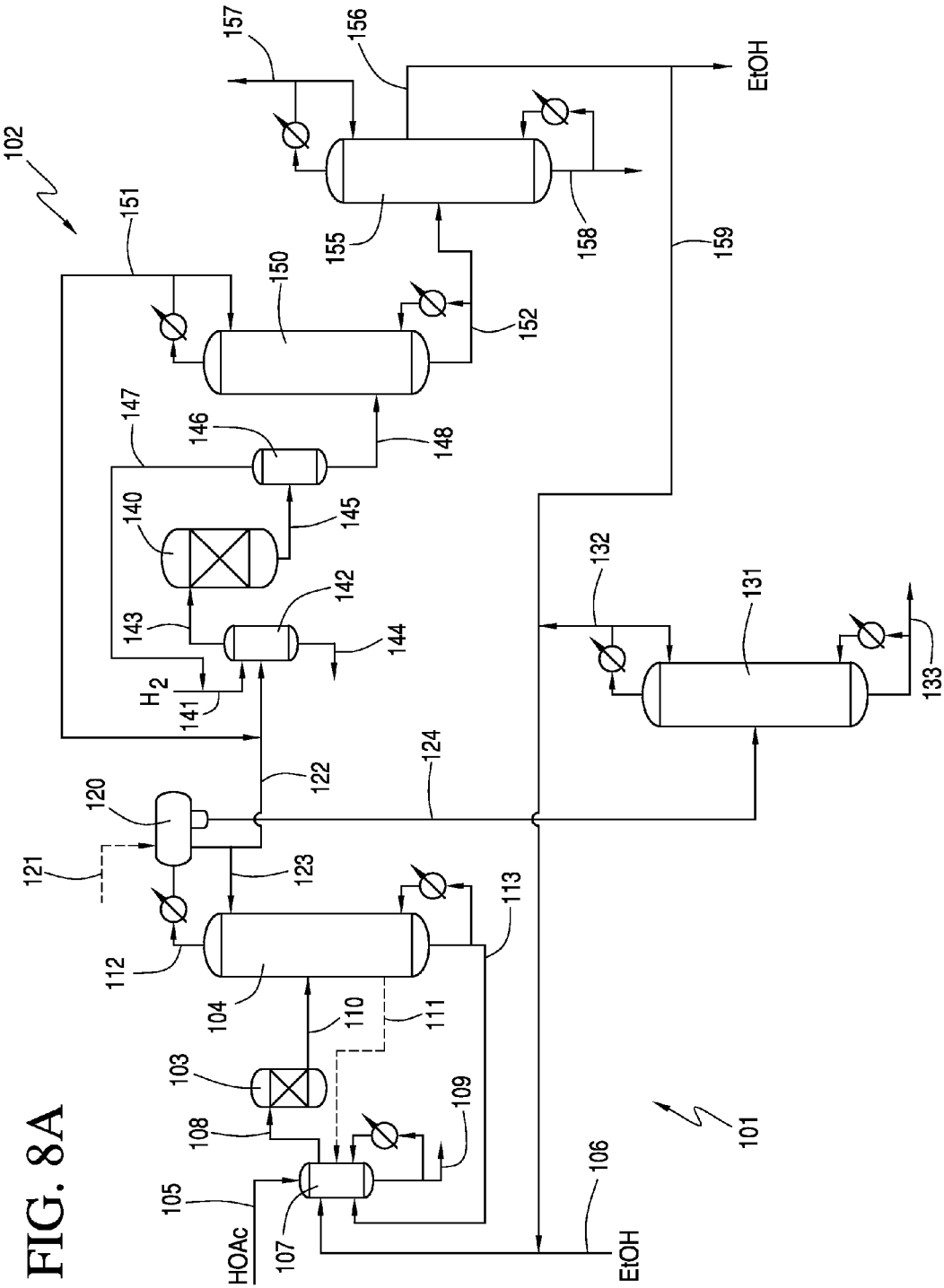
FIG. 8A is a schematic diagram of ethanol production process having a finishing column in the hydrogenolysis zone in accordance with one embodiment of the present invention.
Figure 8B:
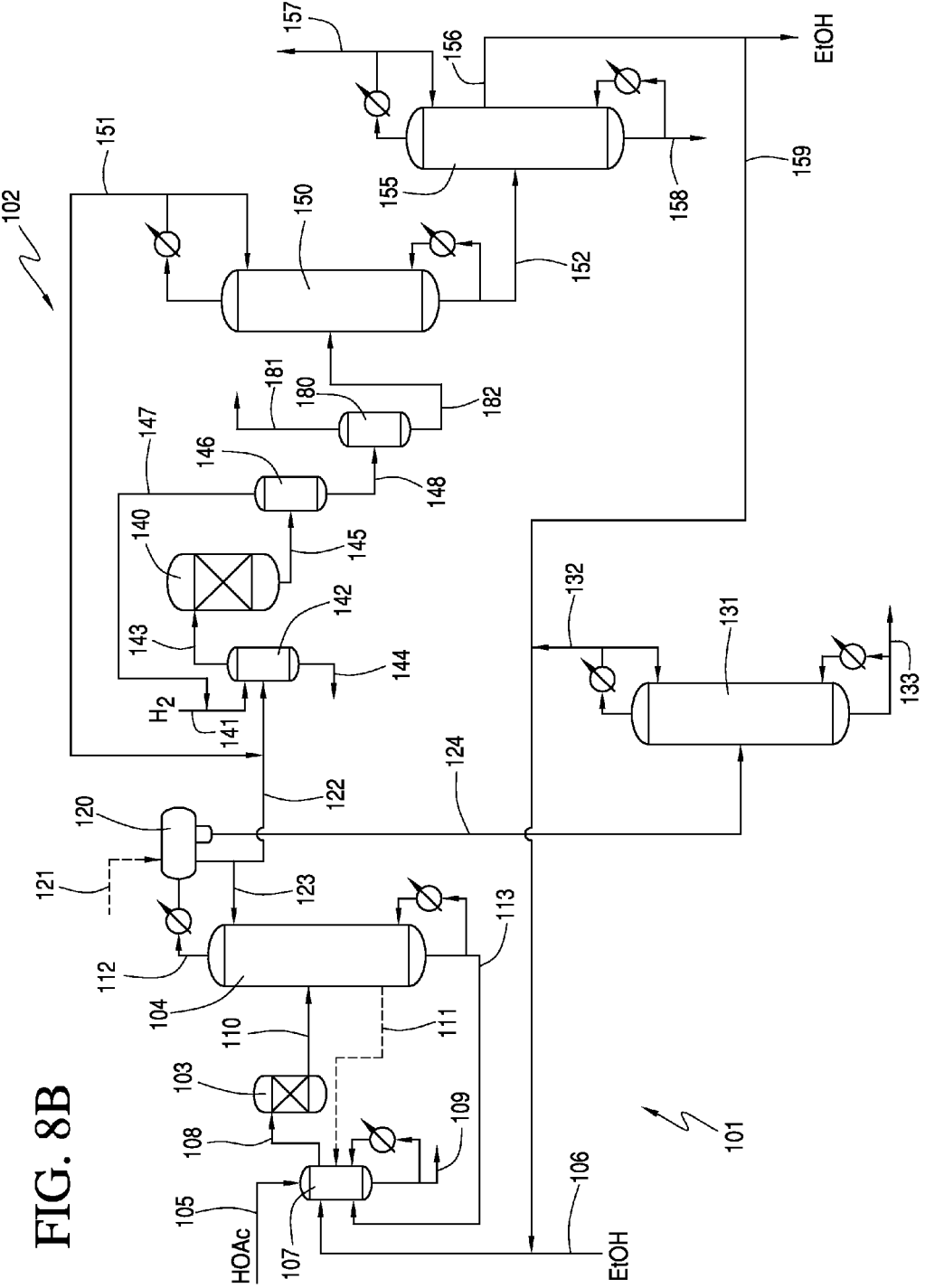
FIG. 8B is a schematic diagram showing multiple flashers in the hydrogenolysis zone in accordance with one embodiment of the present invention.

In one embodiment, the crude reaction mixture in line 145 may be separated using one or more flashers as shown in FIG. 8B. When dual flashers are used, it is preferred to use a high pressure flasher 146 followed by a low pressure flasher 180. The first high pressure flasher 146 operates at the temperature and reaction pressures described above. The second low pressure flasher 180 operates at a temperature from 20° C. to 100° C., e.g., from 30° C. to 85° C. or from 40° C. to 70° C. In one embodiment, the temperature of second flasher 180 preferably is at least 50° C. lower than first flasher 146, e.g., at least 75° C. lower or at least 100° C. lower. The pressure of second flasher 180 preferably is from 0.1 kPa to 1000 kPa, e.g., from 0.1 kPa to 500 kPa or from 0.1 kPa to 100 kPa. In one embodiment, the pressure of second flasher 180 preferably is at least 50 kPa lower than first flasher 146, e.g., at least 100 kPa lower or at least 600 kPa lower. The vapor stream 181 exiting the second flasher 180 may comprise hydrogen and hydrocarbons, which may be purged and/or returned to the reaction zone in a manner similar to that of the first flasher. The liquid stream in line 182 may be fed to the third distillation column 150. Dual flashers may be used in any of the hydrogenolysis zones described herein.

In FIG. 2, the liquid stream 148 from separator 146 is withdrawn and pumped to the side of a third distillation column 150, also referred to as a "light ends column," to yield a third distillate in line 151 comprising ethyl acetate and a third residue in line 152 comprising ethanol. Preferably the distillation column operates to maintain a low concentration of ethyl acetate in the residue, e.g., less than 1 wt. %, less than 0.1 wt. % or less than 0.01 wt. %. The distillate of column 150 preferably is refluxed at a ratio sufficient to maintain low concentrations of ethyl acetate in the residue and minimize ethanol concentrations in the distillate, and reflux ratio may vary from 30:1 to 1:30, e.g., from 10:1 to 1:10 or from 5:1 to 1:5.

Distillation column 150 may be a tray column or packed column. In one embodiment, distillation column 150 is a tray column having from 5 to 110 trays, e.g., from 15 to 90 trays or from 20 to 80 trays. Distillation column 150 operates at a pressure ranging from 20 kPa to 500 kPa, e.g., from 50 kPa to 300 kPa or from 80 kPa to 200 kPa. Without being bound by theory, lower pressures of less than 101 kPa or less than 70 kPa, may further enhance separation of liquid stream 148. Although the temperature of distillation column 150 may vary, when at atmospheric pressure, the temperature of the distillate exiting in line 151 preferably is from 40° C. to 90° C., e.g., from 45° C. to 85° C. or from 50° C. to 80° C. The temperature of the residue exiting in line 152 preferably is from 45° C. to 95° C., e.g., from 50° C. to 90° C. or from 60° C. to 85° C.

Exemplary compositions of the third column 150 are shown in Table 6 below. It should be understood that the distillate and residue may also contain other components, not listed in Table 6.

TABLE 6

THIRD COLUMN 150 (FIG. 2)

|  | Conc. (wt. %) | Conc. (wt. %) | Conc. (wt. %) |
|---|---|---|---|
| Third Distillate |  |  |  |
| Ethyl Acetate | 20 to 80 | 25 to 75 | 30 to 70 |
| Ethanol | 0.01 to 45 | 1 to 35 | 2 to 30 |
| Water | <10 | <5 | <3 |
| Acetaldehyde | 0.01 to 30 | 0.1 to 20 | 1 to 10 |
| Isopropanol | 0.001 to 0.5 | 0.001 to 0.1 | 0.001 to 0.05 |
| Acetone | 0.001 to 3 | 0.001 to 1 | 0.001 to 0.5 |
| Diethyl acetal | 0.001 to 3 | 0.001 to 1 | 0.01 to 0.5 |
| Carbon Gases | 0.001 to 2 | 0.001 to 1 | 0.001 to 0.5 |
| Third Residue |  |  |  |
| Ethanol | 80 to 99.5 | 85 to 99.5 | 90 to 99.5 |
| Water | <20 | 0.001 to 15 | 0.01 to 10 |
| Ethyl Acetate | <0.01 | <0.001 | <0.0001 |
| Isopropanol | 0.001 to 3 | 0.001 to 1 | 0.001 to 0.5 |
| Acetone | 0.001 to 3 | 0.001 to 1 | 0.001 to 0.5 |
| Diethyl acetal | 0.001 to 3 | 0.001 to 1 | 0.01 to 0.5 |
| 2-butanol | 0.001 to 3 | 0.01 to 1 | 0.01 to 0.5 |
| n-butanol | <1 | <0.5 | <0.1 |
| Heavies | <1 | <0.5 | <0.1 |

Without being bound by theory, the presence of acetaldehyde in the crude reaction mixture from the hydrogenolysis reactor may produce several different impurities. The heavy impurities, such as higher alcohols, may build up in the third residue. In particular, 2-butanol has been found to be an impurity in this process. The weight ratio of 2-butanol to n-butanol in the third residue may be greater than 2:1, e.g., greater than 3:1 or greater than 5:1. Depending on the intended use of ethanol, these impurities may be of less significance. However, when a purer ethanol product is desired, a portion of third residue may be further separated in a finishing column 155 as described below in FIG. 8.

1. Third Distillate to Recycle to Hydrogenolysis Section

Third distillate in line 151 may comprise ethyl acetate and/or ethanol. In one embodiment, as shown in FIGS. 2-6, 8 and 9, third distillate in line 151 may be returned, directly or indirectly, to hydrogenolysis reactor 140. When hydrogenolysis reactor 140 operates at a lower ethyl acetate conversion, e.g. less than 90% conversion, less than 85% conversion or less than 70% conversion, it may be possible to recycle ethyl acetate back to hydrogenolysis reactor 140. Third distillate in line 151 is condensed and combined with the ester feed stream and co-fed to vaporizer 142. This produces a distillate having a molar ratio of ethanol to ethyl acetate, of approximately 1:1. Advantageously, this embodiment may avoid recycling ethanol through hydrogenolysis reactor 140 that may lead to capacity restraints and additional capital costs. When returning third distillate to hydrogenolysis reactor 140, it is preferred to operate column 150 with a design and under conditions that minimize the ethanol to ethyl acetate ratio, e.g., distillation trays and/or reflux ratio.

In one embodiment, third distillate in line 151 may comprise other organic compounds such as aldehydes. Recycling the aldehydes to the esterification reactor 103, may cause aldol condensation and result in the production of other byproducts. However, recycling a third distillate in line 151 that contains aldehydes to hydrogenolysis reactor 140 tends to produce additional ethanol.

Third residue in line 152 may be withdrawn as the product. In one embodiment, shown in FIGS. 2-6, a portion of third residue in line 152 is separated into an ethanol return stream 153. Ethanol return stream 153 is fed to esterification zone 101. When reducing ethyl acetate in the presence of hydrogen, two moles of ethanol are formed. Thus, it may be feasible to return a portion of the ethanol to the esterification to produce additional ethyl acetate while still producing ethanol product.

Because ethanol return stream 153 is deficient in ethyl acetate for the purposes of azeotroping water in the overhead of first column 104, it may be necessary to combine ethanol return stream 153 with at least one ethyl acetate containing stream from the esterification separation processes. This will allow an azeotrope agent to be added to first column 104, as shown in FIG. 2. In some embodiments, the azeotrope agent may be directly added by passing through vaporizer 107 and reactor 103. For example, as shown in FIG. 2, second distillate 132 of recovery column 131 may be combined with the ethanol return stream 153. In other embodiments, the azeotrope agent may be added directly from an outside source to first column 104.

2. Third Distillate to Recycle Esterification Zone

Figure 7:
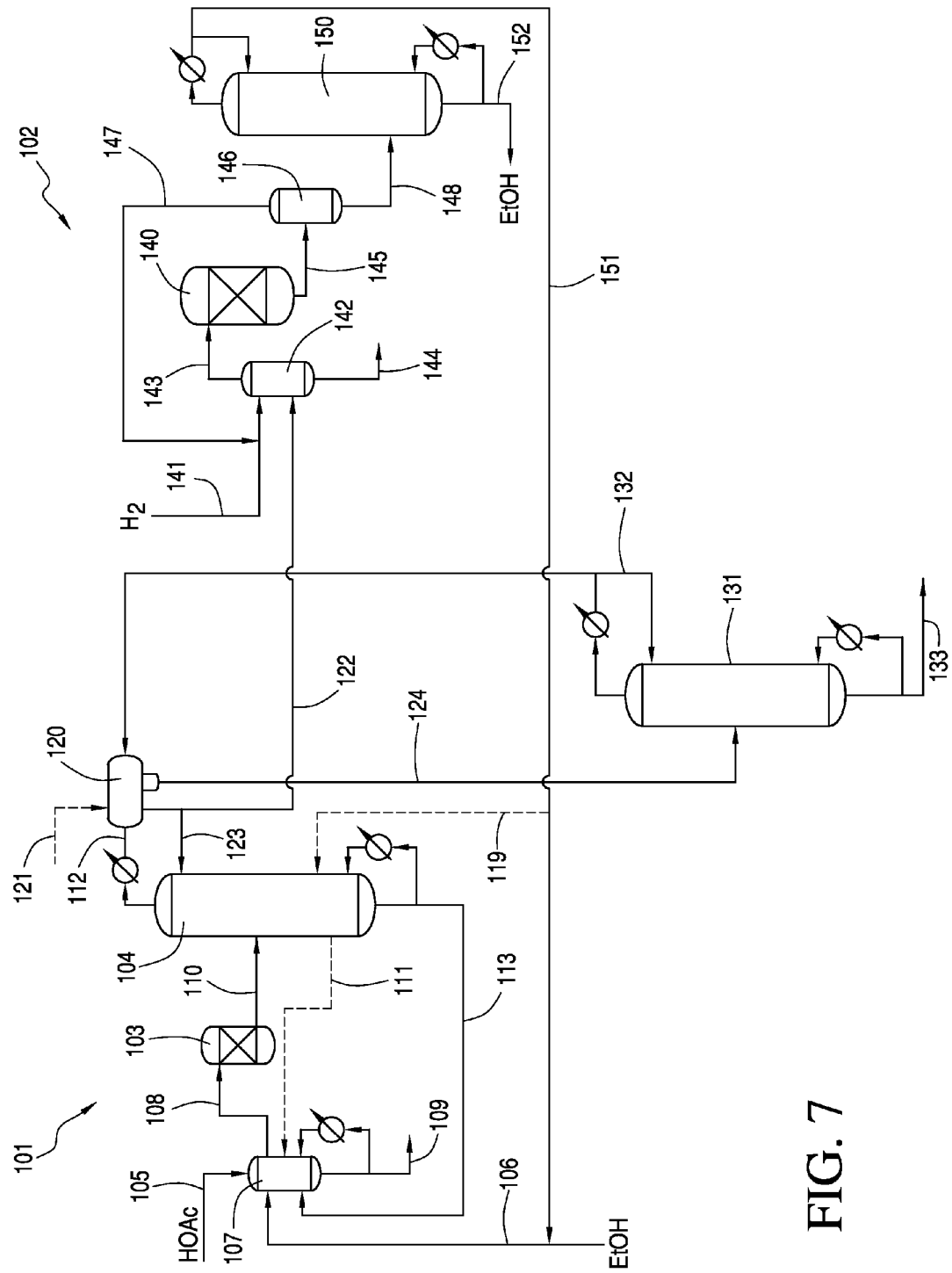
FIG. 7 is a schematic diagram of ethanol production process where the distillate of the light ends column in the hydrogenolysis unit is fed to the esterification zone in accordance with one embodiment of the present invention.

In another embodiment, as shown in FIG. 7, third distillate in line 151 may be returned, directly or indirectly, to esterification zone 101. Third distillate in line 151 may be combined with either the acetic acid feed stream in line 105 or ethanol feed stream in line 106. When third distillate 151 is returned to esterification reactor 103, it may be possible to return a relatively larger amount of ethanol. Optionally, third distillate in line 151 may be split and a portion may be fed to esterification reactor 103 and another portion to first column 104 via optional line 119. In addition, the conversion of ethyl acetate in the hydrogenolysis reactor 140 may be greater than 70%, e.g., greater than 85% or greater than 90%. This also allows third column to operate under less stringent conditions, e.g., with a lower reflux ratio. In addition, when an appreciable amount of alcohols having more than at least 4 carbons, such as n-butanol and/or 2-butanol, are produced through side reactions in the hydrogenolysis reactor 140, it is preferred not to return these higher alcohols to the esterification step as the higher alcohols may react with acetic acid leading to a buildup of higher acetates in the process.

Third distillate in line 151 may have a higher ethanol to ethyl acetate ratio when directing this stream to esterification zone 101 as compared to the ethanol to ethyl acetate ratio when recycling back to hydrogenolysis zone 102. The additional ethyl acetate from the third distillation column 150 may provide for an azeotrope agent to first column 104. In addition, the ethanol in the third distillate may be used to further esterify the acetic acid. In such embodiments, as shown in FIG. 7, preferably none of the third residue in line 152 is returned to esterification zone. In addition, because the third distillate may comprise ethanol and ethyl acetate, it may not be necessary to add second distillate 132 thereto. Thus, second distillate 132 may be returned to overhead decanter 120 as shown in FIG. 7.

Depending on the concentration of ethanol in third distillate in line 151, it may be optional to dilute the third distillate in line 151 with a portion of the third residue in line 152. Although it may be preferred to remove the ethanol to be used in esterification zone 101 via third distillate 151, in some embodiments, the process may require additional ethanol to be sent to esterification zone 101. In some embodiments, less than 20% of the third residue in line 152 may be combined with third distillate in line 151 and returned to esterification zone 101. More preferably less than 15% of the third residue in line 152 or less than 5% of the third residue in line 152.

3. Finishing Column

In some embodiments, it may be necessary to further treat the third residue to remove additional heavy compounds such as higher alcohols and any light components from the ethanol.

Figure 9A:
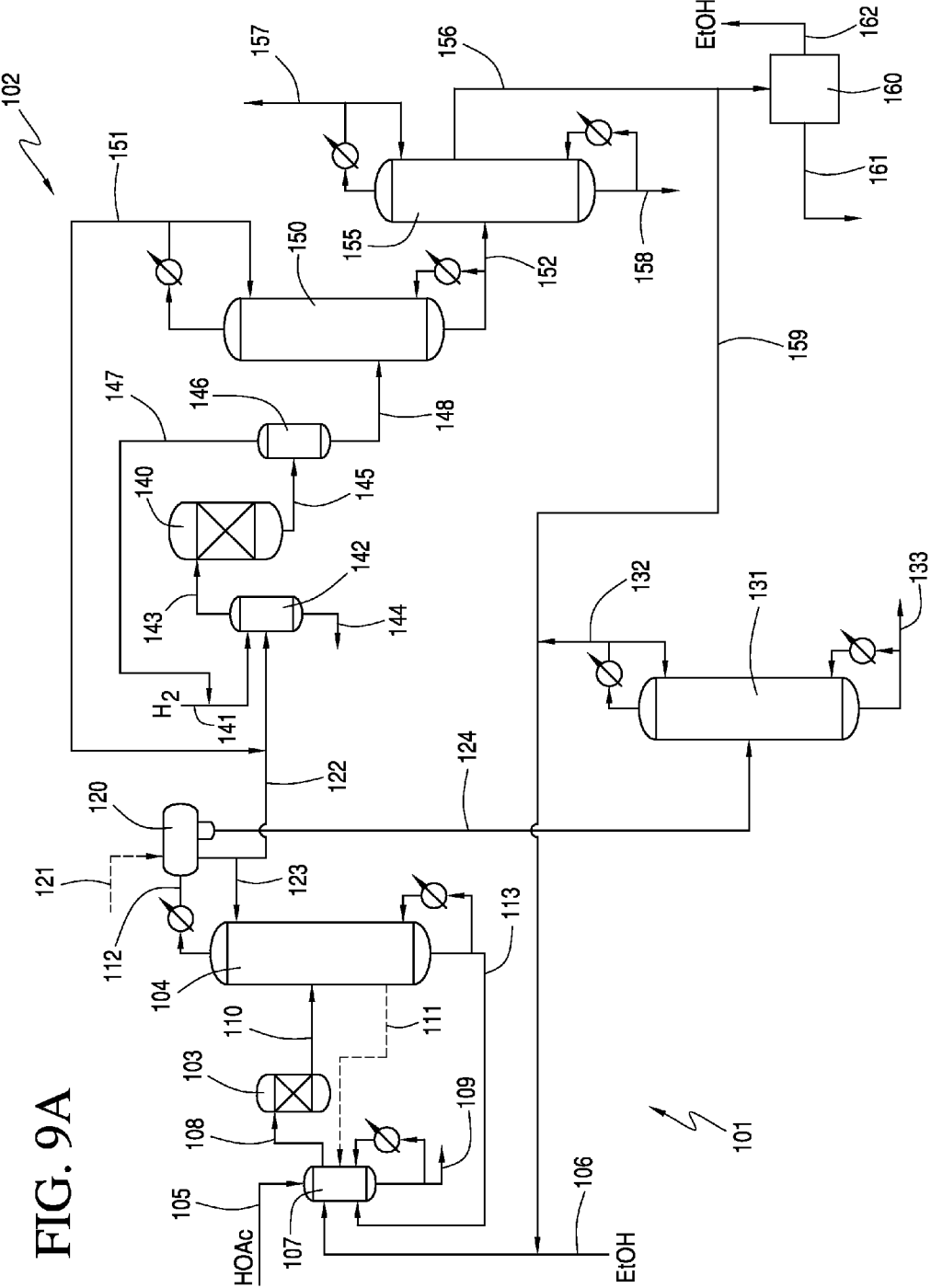
FIG. 9A is a schematic diagram of ethanol production process having a water separator for the ethanol product in the hydrogenolysis zone in accordance with one embodiment of the present invention.

As shown in FIGS. 8A, 8B, and 9A, there is provided a finishing column 155, also referred to as a "fourth column." Third residue in line 152 is fed to a lower portion of fourth column 155. Fourth column 155 produces an ethanol sidestream in line 156, a fourth distillate in line 157 and a fourth residue in line 158. Preferably ethanol sidestream 156 is the largest stream withdrawn from fourth column 155 and is withdrawn at a point above the feed point of the third residue in line 152. In one embodiment the relative flow ratios of sidestream to residue is greater than 50:1, e.g., greater than 100:1 or greater than 150:1.

Ethanol sidestream 156 preferably comprises at least 90% ethanol, e.g., at least 92% ethanol and a least 95% ethanol. Depending on the amount of water fed to hydrogenolysis reactor 140, the water concentration in ethanol sidestream 156 may be less than 10 wt. %, e.g., less than 5 wt. % or less than 1 wt. %. In addition, the amount of other impurities, in particular diethyl acetal and 2-butanol, are preferably less than 0.05 wt. %, e.g., less than 0.03 wt. % or less than 0.01 wt. %. The fourth distillate in line 157 preferably comprises a weight majority of the diethyl acetal fed to fourth column 155. In addition, other light components, such as acetaldehyde and/or ethyl acetate may also concentrate in the fourth distillate. The fourth residue in line 158 preferably comprises a weight majority of the 2-butanol fed to fourth column 155. Heavier alcohols may also concentrate in the fourth residue in line 158.

Fourth column 155 may be a tray column or packed column. In one embodiment, Fourth column 155 is a tray column having from 10 to 100 trays, e.g., from 20 to 80 trays or from 30 to 70 trays. Fourth column 155 operates at a pressure ranging from 1 kPa to 510 kPa, e.g., from 10 kPa to 450 kPa or from 50 kPa to 350 kPa. Although the temperature of fourth column 155 may vary, the temperature of the residue exiting in line 158 preferably is from 70° C. to 105° C., e.g., from 70° C. to 100° C. or from 75° C. to 95° C. The temperature of the fourth distillate exiting in line 157 preferably is from 50° C. to 90° C., e.g., from 55° C. to 85° C. or from 65° C. to 80° C. Ethanol sidestream 156 is preferably withdrawn at the boiling point of ethanol, about 78° C. at atmospheric pressure.

As shown in FIGS. 8A and 8B, a portion of the third distillate in line 151 is returned to hydrogenolysis zone 102 and a portion of ethanol sidestream 156 in line 159 may be returned to esterification zone 101. In one embodiment, less than half of the ethanol sidestream 156, i.e., less than 50%, less than 40%, or less than 20%, is returned via line 159. Returning ethanol in line 159 may reduce the amount of heavy compounds that are returned to esterification zone 101.

In some embodiments, a portion of the fourth residue, sidestream or fourth distillate may be dehydrated to form aliphatic alkenes. In one embodiment, the 2-butanol in the fourth residue may be dehydrated to 2-butene. In another embodiment, the 2-butanol in the fourth residue stream may be recovered in a separate system.

In one embodiment, instead of purging the fourth distillate in line 157 or the fourth residue in line 158, a portion thereof may be fed to vaporizer 107. Heavy ends compounds may be removed in the blowdown stream 109.

The ethanol product, either obtained as the third residue in FIGS. 2-7 or the sidestream in FIGS. 8A and 8B, may contain small concentrations of water. For some ethanol applications, in particular for fuel applications, it may be desirable to further reduce the water concentration. As shown in FIG. 9A, a portion of ethanol sidestream 156 is fed to a water separation unit 160. Water separation unit 160 may include an adsorption unit, one or more membranes, molecular sieves, extractive distillation units, or a combination thereof. Ethanol sidestream 156 may be withdrawn as a vapor or liquid stream, but it may be more suitable to use a vapor stream. Suitable adsorption units include pressure swing adsorption (PSA) units and thermal swing adsorption (TSA) units. In FIG. 9A, a PSA unit 160 may be employed to remove water from the sidestream 156. PSA unit 160 is operated at a temperature from 30° C. to 160° C., e.g., from 80° C. to 140° C., and a pressure of from 0.01 kPa to 550 kPa, e.g., from 1 kPa to 150 kPa. The PSA unit may comprise two to five beds. The water stream 161 may be purged and/or directed to recovery column 131. The resulting dried ethanol product stream 162 preferably has a water concentration that is less than 1 wt. %, e.g., less than 0.5 wt. % or less than 0.1 wt. %. The ethanol returned to esterification zone 101 may be separated in line 159 prior to PSA unit 160 to increase the capacity of the water separation unit. This allows an impure ethanol recycle and does not require additional capital to purify the ethanol prior to returning the ethanol to esterification zone 101.

Figure 9B:
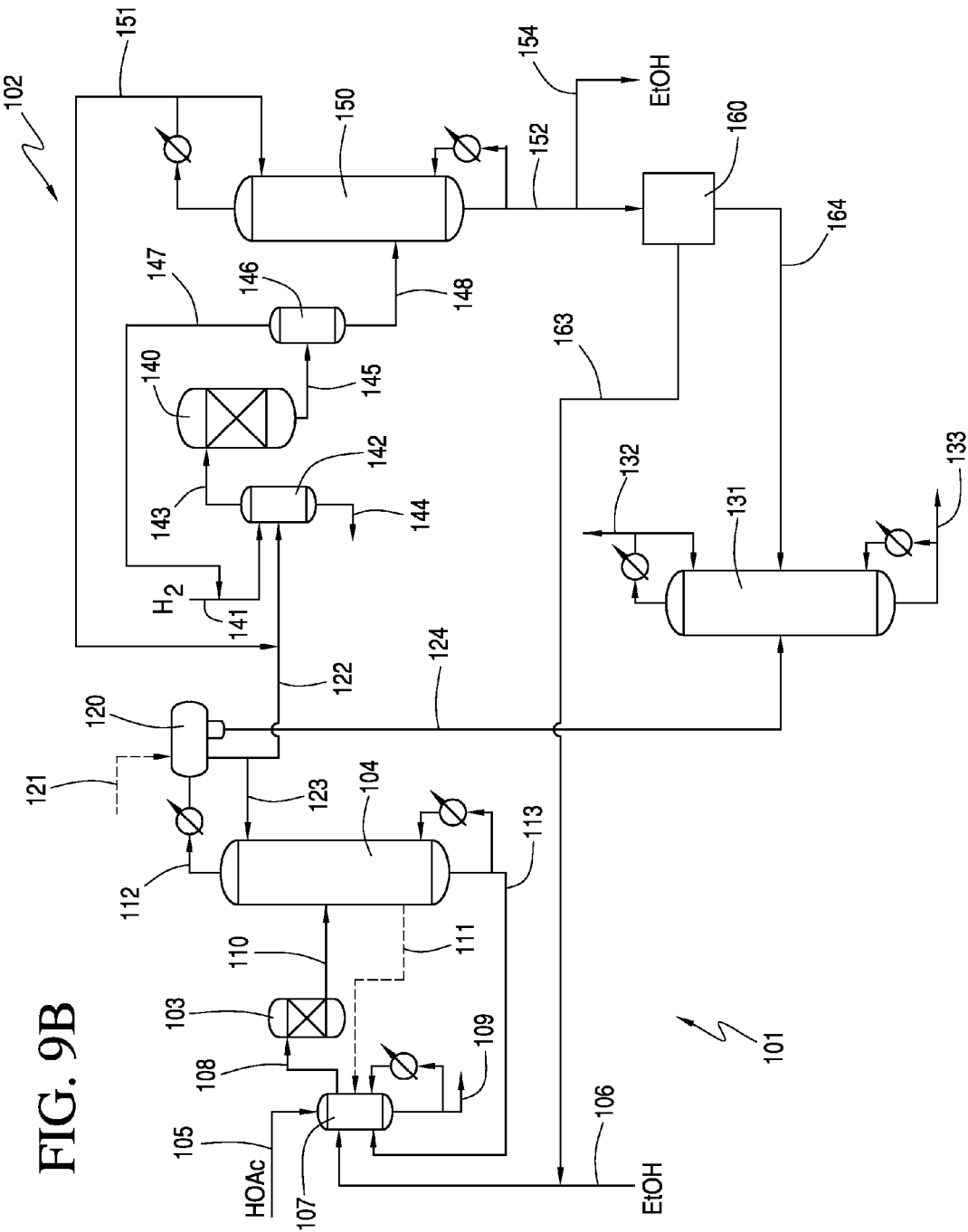
FIG. 9B is a schematic diagram showing a water separator for an ethanol return to the esterification zone in accordance with one embodiment of the present invention.

In FIG. 9B, a water separation unit 160 may remove the water from a portion of the third residue in line 152 comprising ethanol. Depending on the ethanol application, the water concentration in third residue in line 152 may be sufficiently low and an ethanol product may be recovered in line 154. However, the water concentration may be too large to be recycled to esterification zone 101. Water separation unit 160 removes a majority of the water in the third residue in line 152 to produce a dry ethanol return stream 163 and a water stream 164. Dry ethanol return stream 163 has a water concentration that is less than 1 wt. %, e.g., less than 0.5 wt. % or less than 0.1 wt. % and may be returned to esterification zone 101. Water stream 164 may be purged or fed to recovery column 131 to remove any organics, including ethanol, prior to purging. The distillate in line 132 may be combined with dry ethanol return stream 163 or fed to decanter 120.

In some embodiments, the desired ethanol product is an anhydrous ethanol that is suitable for use as a fuel or as a blend for other fuels, such as gasoline. Water separation unit 160 as described herein may be suitable for producing anhydrous ethanol.

Figure 10A:
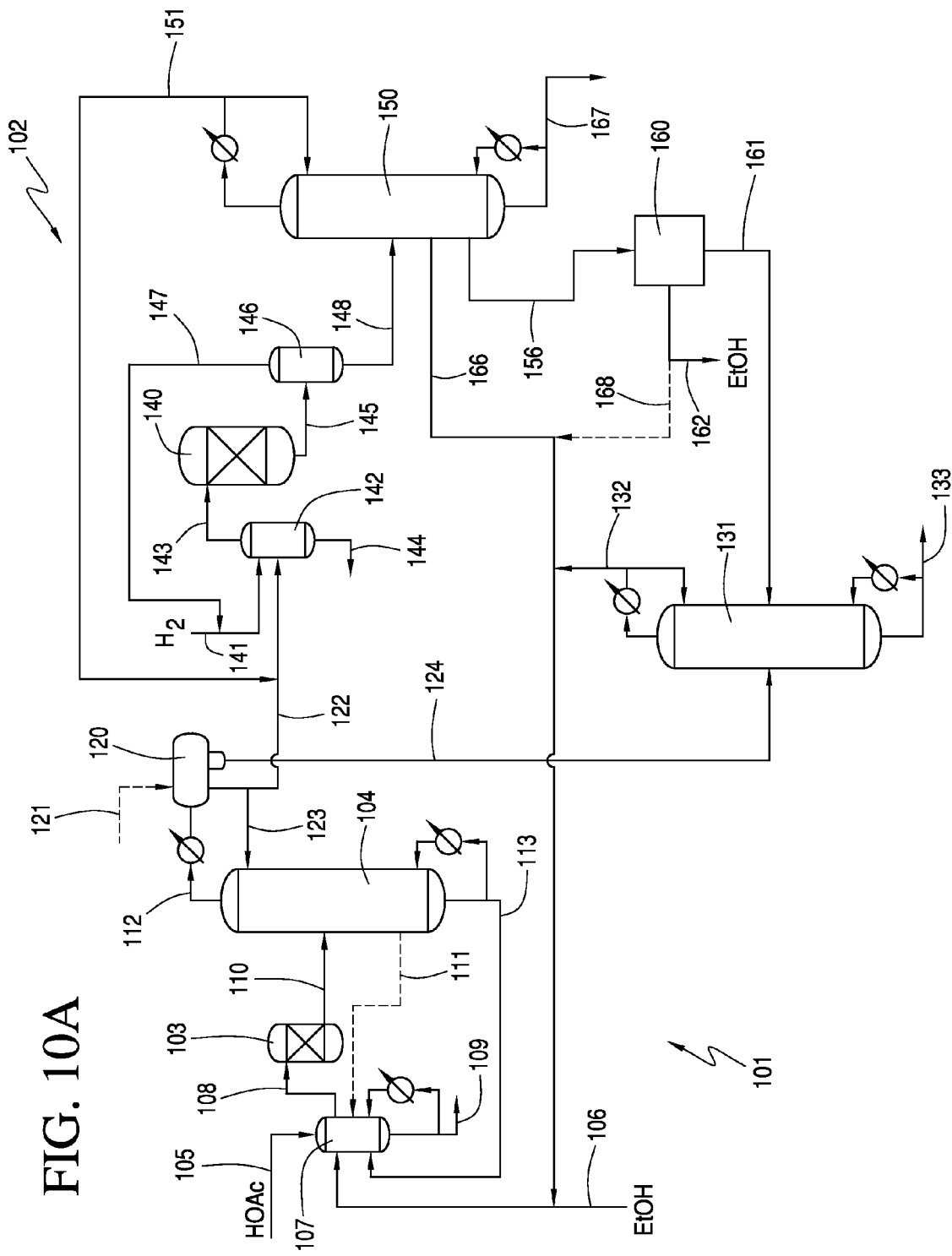
FIG. 10A is a schematic diagram showing a water separator for producing anhydrous ethanol in accordance with one embodiment of the present invention.
Figure 10B:
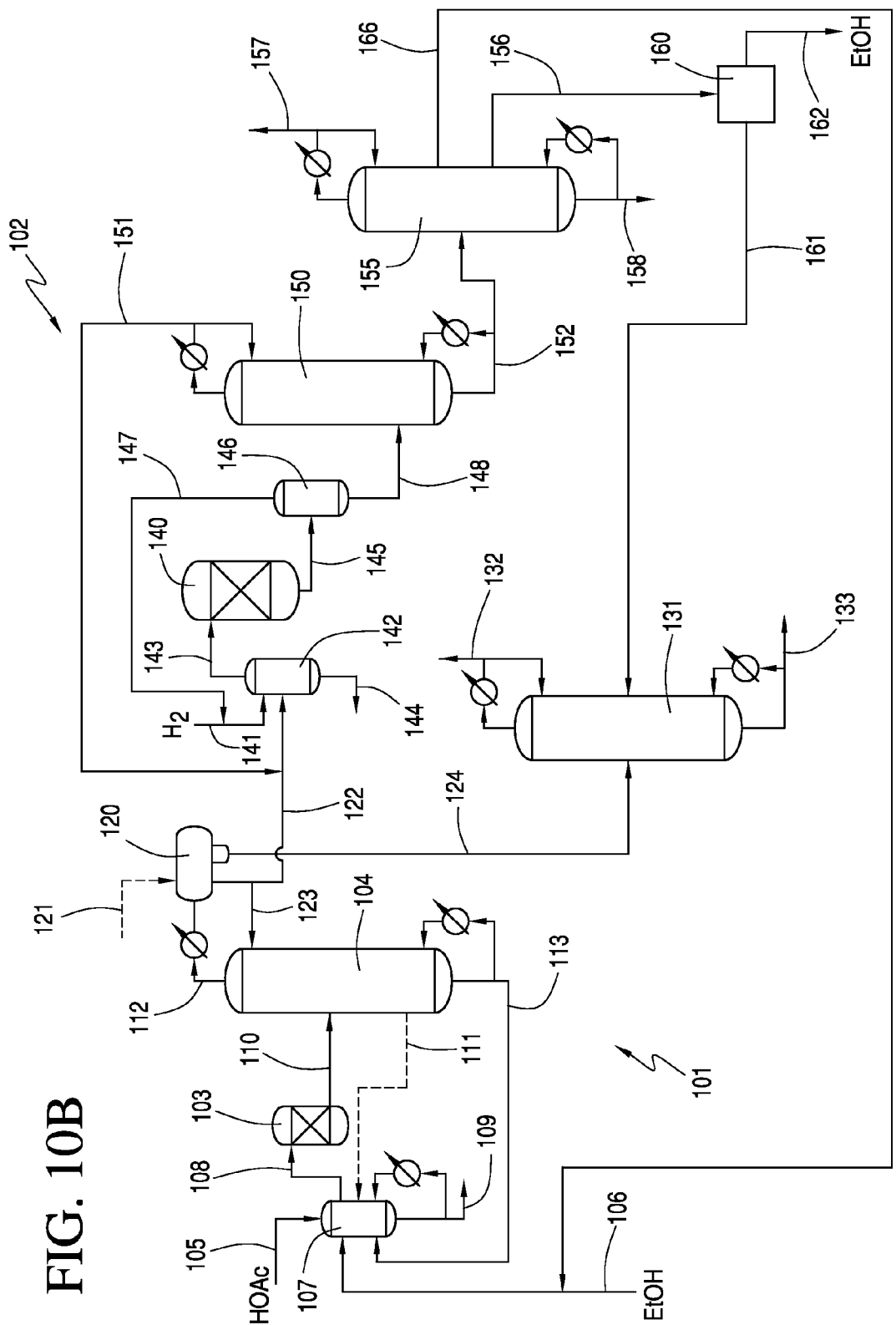
FIG. 10B is a schematic diagram of ethanol production having separate liquid ethanol recycle and water separator for the ethanol product in the hydrogenolysis zone in accordance with one embodiment of the present invention.

In one embodiment, in may be preferable to return a liquid ethanol stream 166 to the esterification zone 101. Thus, only the ethanol to be produced as anhydrous ethanol is subsequently dried, which may reduce the capital and energy requirements. FIGS. 10A and 10B are schematics in which liquid ethanol stream 166 and ethanol sidestream 156 are withdrawn. Preferably, ethanol sidestream 156 is a vapor sidestream that may be directly fed to a pressure swing adsorption unit or membrane to remove water. In one embodiment, ethanol sidestream 156 may be taken near the reboiler of the respective column to allow a single stage flashing to remove heavy components that may be present. Liquid ethanol stream 166 may comprise ethanol, ethyl acetate, water and/or mixtures thereof. The ethyl acetate may be suitable as an azeotrope for esterification zone 101. Preferably, liquid ethanol stream 166 may comprise less water than ethanol sidestream 156 and does not require any additional water separation prior to being returned to esterification zone 101. Liquid ethanol stream 166 may be withdrawn at a point higher in the respective column, but preferably below the feed location(s) to the column. In FIG. 10A, liquid ethanol stream 166 and ethanol sidestream 156 are withdrawn from third distillation column 150. Advantageously, ethanol sidestream 156 is withdrawn such that heavy components, which may be unsuitable for fuel applications, are removed in third distillation column in the residue. The residue in line 167 of third distillation column 150 contains heavy components, e.g. acetic acid, acetates, and heavy alcohols, such as isopropanol, n-butanol and 2-butanol. The residue in line 167 may be purged. In some embodiments, residue in line 167 may comprise ethanol and/or acetic acid and the residue in line 167 may be returned to vaporizer 107. The heavier components are then removed in the blowdown stream 109. In FIG. 10B, liquid ethanol stream 166 and ethanol sidestream 156 are withdrawn from fourth distillation column 155. Similar to the residue of third distillation column 150, the residue in line 158 from fourth distillation column 155 may also be purged or returned to vaporizer 107.

Ethanol sidestream 156 is preferably a vapor stream that is directed to water separation unit 160 to yield a water stream 161 and dried ethanol product stream 162. Water separation unit 160 may include an adsorption unit, one or more membranes, molecular sieves, extractive distillation units, or a combination thereof. More preferably, water separation unit 160 may be a pressure swing adsorption unit. The vapor ethanol sidestream 156 may comprise less than 10 wt. % water, e.g., less than 8 wt. % or less than 5 wt. %. Water separation unit 160 removes at least 85% of the water in ethanol sidestream 156, e.g. at least 90% or at least 95%. The resulting dried ethanol product stream 162 may have a water concentration that is less than 2 wt. %, e.g. less than 1 wt. %. or less than 0.5 wt. %. Dried ethanol product stream 162 may be used as a fuel-grade ethanol and may be blended with gasoline.

A wet ethanol stream 161 is also obtained from water separation unit 160 directed to recovery column 131 to recover any ethanol. The ethanol from wet ethanol stream 161 may be returned via the distillate in line 132 to esterification zone 101. Optionally, a portion of dried ethanol product in line 168 may be combined with the liquid ethanol stream 166 and returned to esterification zone 101.

The columns shown in the figures may comprise any distillation column capable of performing the desired separation and/or purification. For example, unless described otherwise, the columns may be tray columns having from 1 to 150 trays, e.g., from 10 to 100 trays, from 20 to 95 trays or from 30 to 75 trays. The trays may be sieve trays, fixed valve trays, movable valve trays, or any other suitable design known in the art. In other embodiments, a packed column may be used. For packed columns, structured packing or random packing may be employed. The trays or packing may be arranged in one continuous column or may be arranged in two or more columns such that the vapor from the first section enters the second section while the liquid from the second section enters the first section, etc.

The associated condensers and liquid separation vessels that may be employed with each of the distillation columns may be of any conventional design and are simplified in the figures. Heat may be supplied to the base of each column or to a circulating bottom stream through a heat exchanger or reboiler. Other types of reboilers, such as internal reboilers, may also be used. The heat that is provided to the reboilers may be derived from any heat generated during the process that is integrated with the reboilers or from an external source such as another heat generating chemical process or a boiler. Although one reactor and one flasher are shown in the figures, additional reactors, flashers, condensers, heating elements, and other components may be used in various embodiments of the present invention. As will be recognized by those skilled in the art, various condensers, pumps, compressors, reboilers, drums, valves, connectors, separation vessels, etc., normally employed in carrying out chemical processes may also be combined and employed in the processes of the present invention.

The temperatures and pressures employed in the columns may vary. Temperatures within the various zones will normally range between the boiling points of the composition removed as the distillate and the composition removed as the residue. As will be recognized by those skilled in the art, the temperature at a given location in an operating distillation column is dependent on the composition of the material at that location and the pressure of column. In addition, feed rates may vary depending on the size of the production process and, if described, may be generically referred to in terms of feed weight ratios.

For purposes of the present invention, exemplary ethanol compositional ranges are provided below in Table 7. Depending on the application of the ethanol, one or more of the other organic impurities listed in Table 7 may be present.

TABLE 7

FINISHED ETHANOL COMPOSITIONS

| Component | Conc. (wt. %) | Conc. (wt. %) | Conc. (wt. %) |
|---|---|---|---|
| Ethanol | 75 to 99.9 | 88 to 99.5 | 90 to 96 |
| Water | <12 | 0.01 to 7.5 | 0.5 to 5 |
| Acetic Acid | <0.1 | <0.01 | <0.005 |
| Ethyl Acetate | <0.1 | <0.01 | <0.005 |
| Isopropanol | <0.5 | <0.1 | <0.05 |
| Diethyl Acetal | <0.5 | <0.1 | <0.05 |
| n-butanol | <0.5 | <0.1 | <0.05 |
| 2-butanol | <2 | <0.5 | <0.1 |
| Acetone | <0.5 | <0.1 | <0.05 |

In one embodiment, the recovered ethanol may have a composition that is from 92 wt. % to 97 wt. % ethanol, 3 wt. % to 8 wt. % water, 0.01 wt. % to 0.2 wt. % 2-butanol, and 0.02 wt. % to 0.08 wt. % isopropanol. The amount of 2-butanol may be greater than isopropanol. Preferably, other than 2-butanol and isopropanol, the recovered ethanol comprises less than 1 wt. % of one or more organic impurities selected from the group consisting of acetaldehyde, acetic acid, diethyl acetal, and ethyl acetate. The 2-butanol concentration in the ethanol sidestream may be reduced to an amount that is less than 0.01 wt. % when using a finishing column.

IV. Uses of Ethanol

Ethanol produced by the embodiments of the present invention may be used in a variety of applications including fuels, solvents, chemical feedstocks, pharmaceutical products, cleansers, sanitizers, hydrogen transport or consumption. In fuel applications, ethanol may be blended with gasoline for motor vehicles such as automobiles, boats and small piston engine aircraft. In non-fuel applications, ethanol may be used as a solvent for toiletry and cosmetic preparations, detergents, disinfectants, coatings, inks, and pharmaceuticals. Ethanol may also be used as a processing solvent in manufacturing processes for medicinal products, food preparations, dyes, photochemicals and latex processing.

Ethanol may also be used as a chemical feedstock to make other chemicals such as vinegar, ethyl acrylate, ethyl acetate, ethylene, glycol ethers, ethylamines, ethyl benzene, aldehydes, butadiene, and higher alcohols, especially butanol. In the production of ethyl acetate, ethanol may be esterified with acetic acid. In another application, ethanol may be dehydrated to produce ethylene. Any known dehydration catalyst can be employed to dehydrate ethanol, such as those described in copending U.S. Pub. Nos. 2010/0030002 and 2010/0030001, the entire contents and disclosures of which are hereby incorporated by reference. A zeolite catalyst, for example, may be employed as the dehydration catalyst. Preferably, the zeolite has a pore diameter of at least about 0.6 nm, and preferred zeolites include dehydration catalysts selected from the group consisting of mordenites, ZSM-5, a zeolite X and a zeolite Y. Zeolite X is described, for example, in U.S. Pat. No. 2,882,244 and zeolite Y in U.S. Pat. No. 3,130,007, the entireties of which are hereby incorporated herein by reference.

In order that the invention disclosed herein may be more efficiently understood, examples are provided below. It should be understood that these examples are for illustrative purposes only and are not to be construed as limiting the invention in any manner.

EXAMPLES

Example 1

Vapor-Phase Esterification

Vapor-phase reactor feed mixtures of acetic acid (HOAc) and ethanol (EtOH) were passed over Amberlyst™ 36 ion-exchange resin (IER) catalyst (Rohm & Haas) in plug-flow tubular reactor at reaction temperatures in a range of 110° C. to 130° C., with an operating pressure of 101 kPa. The ion-exchange resin was diluted with 1 mm glass beads at a 2:1 dilution ratio. Liquid flow rates to the vaporizer were 6.7+/− 0.2 g/minute. The vapor-phase reactor feed mixtures contained excess molar acetic acid concentrations in an acetic acid/ethanol molar ratio range of from 1.07:1 to 2:1. The observed conversions of ethanol ranged from 88.9% to 94.9% as shown in Table 8. EtOAc is an abbreviation for ethyl acetate.

TABLE 8

| | 1 | 2 | 3 | 4 | 5 | 6 | 7 | 8 |
|---|---|---|---|---|---|---|---|---|
| Mole Ratio (HOAc to EtOH) | 1.07 | 1.07 | 1.07 | 1.50 | 1.50 | 1.50 | 2.00 | 2.00 |
| IER Catalyst Volume (mL) | 60 | 60 | 60 | 60 | 60 | 60 | 60 | 60 |
| Reactor Temperature (° C.) | 110 | 120 | 130 | 110 | 120 | 130 | 120 | 130 |
| Combined Feed Rate (g/min) | 6.5 | 6.8 | 6.9 | 6.5 | 6.8 | 6.9 | 6.6 | 6.6 |
| Conversion of EtOH (%) | 88.9 | 90.4 | 89.5 | 90.9 | 92.6 | 93.1 | 94.6 | 94.9 |
| EtOAc STY (moles EtOAc/L cat/hr) | 47.0 | 48.3 | 50.3 | 45.0 | 44.9 | 44.7 | 37.8 | 39.3 |

Example 2

Vapor-Phase Esterification at 3:1 Molar Ratio

Similar to Example 1, vapor-phase mixtures of acetic acid and ethanol were passed over 60 ml Amberlyst™ 36 ion-exchange resin catalyst at reaction temperatures in a range of from 120 to 130° C. at an operating a pressure of 101 kPa. An reactor feed acetic acid to ethanol mole ratio of 3:1 liquid mixture was fed to the vaporizer at liquid flow rates in a range from 15.7 to 20.1 g/minute. The observed conversions of ethanol ranged from 93% to 95.3% with ethyl acetate productivities in a range of from 69.2 to 85.3 moles/L cat/hr.

TABLE 9

|  | 9 | 10 | 11 | 12 |
|---|---|---|---|---|
| IER Catalyst Volume (mL) | 60 | 60 | 60 | 60 |
| Reactor Temperature (° C.) | 120 | 130 | 120 | 130 |
| Feed Rate (g/min) | 15.7 | 15.7 | 20.1 | 19.5 |
| EtOAc STY (moles EtOAc/L cat/hr) | 69.2 | 69.3 | 76.9 | 85.3 |
| Conversion of EtOH (%) | 95.0 | 95.3 | 95.2 | 93.0 |

Example 3

Reduced Diethyl Ether Formation

A series of vapor-phase acetic acid esterification reactions with ethanol were passed over 60 ml of Amberlyst™ 36 ion-exchange resin catalyst at LHSV values in a range of from 10.4 to 10.7 hr$^{-1}$), with reaction temperatures in a range from 110° C. to 130° C. When at feed mixture of acetic acid/ethanol mole ratios of 1:1 or 1.2:1, the expected temperature effect on diethyl ether formation is shown in Runs 13-18. When the mole ratio is increased to 1.5:1, surprisingly and unexpectedly, there is a reduced diethyl ether formation regardless of the temperature effect. Table 10 summarizes the results.

TABLE 10

|  | 13 | 14 | 15 | 16 | 17 | 18 | 19 | 20 | 21 |
|---|---|---|---|---|---|---|---|---|---|
| LHSV, hr–1 | 10.7 | 10.7 | 10.7 | 10.5 | 10.5 | 10.5 | 10.4 | 10.4 | 10.4 |
| HOAc/EtOH molar ratio | 1.0 | 1.0 | 1.0 | 1.2 | 1.2 | 1.2 | 1.5 | 1.5 | 1.5 |
| Reaction Temperature (° C.) | 110 | 120 | 130 | 110 | 120 | 130 | 110 | 120 | 130 |
| Diethyl ether (wt %) | 0.222 | 0.65 | 1.45 | 0 | 0 | 0.533 | 0 | 0 | 0 |

Example 4

Hydrogenolysis Catalyst

The hydrogenolysis was carried out in a vapor-phase, heterogeneously catalyzed, continuously stirred tank (Berty type) reactor. The catalyst was T-2130™ (Süd Chemie), which has the following composition: CuO (26%), ZnO (53%). The hydrogenolysis catalyst was reduced at an operating pressure of 690 kPa with an initial temperature of 120° C. that was increased to 170° C. while introducing a low flow rate of hydrogen gas into a constant inert gas feed stream to the reactor to achieve a hydrogen concentration of 0.5-1.0% $H_2$. The $H_2$ concentration was slowly increased stepwise to 2.2%, 3.5%, 4.0%, 5.0% and 6.0% and then was held at a constant reactor temperature of 215° C.

A mixture of $H_2$ (93.6 mol %), $N_2$ (2.5 mol %), and ethyl acetate (3.9 mol %) was passed over 52.9 g T-2130 catalyst at 260° C., with a pressure of 4140 kPa and GHSV of 6000 hr$^{-1}$. The LHSV was 1.0 hr$^{-1}$. The observed conversion of ethyl acetate was 86.4% with a selectivity to ethanol of 92.0%. The observed productivity of ethanol (g EtOH/kg catalyst/hr) was 510 g EtOH/kg catalyst/hr.

Example 5

Hydrogenolysis Catalyst

Operating under the same conditions as Example 4, a mixture of $H_2$ (84.5 mol %), $N_2$ (9.0 mol %), and ethyl acetate (6.5 mol %) was passed over 52.9 g T-2130 at 240° C., with a pressure of 4140 kPa, GHSV of 1700 hr$^{-1}$, and LHSV at 0.47 hr$^{-1}$. The observed conversion of ethyl acetate was 87.8% and the selectivity to ethanol was 96.4%. The observed productivity of ethanol (g EtOH/kg catalyst/hr) was 290 g EtOH/kg catalyst/hr.

Example 6

Hydrogenolysis Catalyst

MegaMax 700™ (Süd Chemie), which has the following composition: CuO (61%), ZnO (28%), $Al_2O_3$ (10%) was used in place of the T-2130 catalyst in Example 4. The operating conditions were similar as to Example 4. A mixture of $H_2$ (92.0 mol %), $N_2$ (2.7 mol %), and ethyl acetate (5.3 mol %) was passed over 38.72 g MegaMax700™ at 250° C. at an operating pressure of 2410 kPa, a GHSV of 5460 hr$^{-1}$, and a LHSV of 1.3 hr$^{-1}$. The observed conversion of ethyl acetate was 80.1% and the selectivity to ethanol was 85.1%. The observed productivity of ethanol (g EtOH/kg catalyst/hr) was 848 g EtOH/kg catalyst/hr.

Example 7

Hydrogenolysis Catalyst

Operating under the same conditions as Example 6, a mixture of $H_2$ (90.4 mol %), $N_2$ (2.4 mol %), and ethyl acetate (7.2 mol %) was passed over 38.72 g MegaMax700™ at 250° C. at an operating a pressure of 5520 kPa, a GHSV of 6333 hr$^{-1}$, and a LHSV of 2.0 hr$^{-1}$. The observed conversion of ethyl acetate was 81.9% and the selectivity to ethanol was 89.0%. The observed productivity of ethanol (g EtOH/kg catalyst/hr) was 1470 g EtOH/kg catalyst/hr.

Example 8

Heavy Impurities in Hydrogenolysis

MegaMax700™ (38.72 g) was used to catalyze hydrogenolysis reactions with mixtures of $H_2$ and ethyl acetate under operating conditions with reaction temperatures in a range of from 250 to 275° C., pressure ranges of from 350 to 800 psig and GHSV values ranging from 3693 to 6333 hr$^{-1}$. The average conversion of ethyl acetate was 83.7% and the average selectivity to ethanol was 84.2%. Higher alcohols (C₃-C₄) detected in condensed hydrogenolysis reactor product samples included iso-propanol, 2-butanol, and 1-butanol as shown in Table 11.

TABLE 11

|  | 22 | 23 | 24 | 25 | 26 | 27 |
|---|---|---|---|---|---|---|
| Reactor Pressure (psig) | 367 | 356 | 357 | 354 | 816 | 803 |
| Reactor Temperature (° C.) | 250 | 250 | 275 | 275 | 250 | 252 |
| GHSV (1/hr) | 3693 | 5455 | 3684 | 5452 | 5100 | 6333 |
| Ethyl Acetate LHSV (1/hr) | 0.9 | 1.3 | 0.8 | 1.2 | 1.6 | 2.0 |
| Conversion of Ethyl Acetate (%) | 85.7 | 80.1 | 86.9 | 82.9 | 85.0 | 81.9 |
| Selectivity to Ethanol (%) | 80.3 | 85.1 | 78.1 | 83.7 | 89.0 | 89.0 |
| iso-propanol (wt %) | 0.072 | 0.049 | 0.244 | 0.186 | 0.037 | 0.019 |
| 2-butanol (wt %) | 0.561 | 0.484 | 1.83 | 1.50 | 0.403 | 0.332 |
| 1-butanol (wt %) | 0.119 | 0.130 | 0.516 | 0.415 | 0.096 | 0.066 |

Example 9

Reduction of Heavy Impurities

A mix of ethyl acetate (87.6 wt %), ethanol (8.55 wt %), and water (3.8 wt %) was fed to a hydrogenolysis reactor. The liquid was vaporized to form a gaseous stream of $H_2$ (89.2 mol %), $N_2$ (4.0 mol %), EtOAc (5.0 mol %), EtOH (0.8 mol %), and water (0.9 mol %). The gas stream reacted over Mega-Max700™ at 275° C., with a pressure of 2514 kPa and GHSV of 5464 $hr^{-1}$ and the LHSV was 1.3 $hr^{-1}$. The observed conversion of ethyl acetate was 80.4% and the selectivity to ethanol was 94.2%. The observed productivity of ethanol (g EtOH/kg catalyst/hr) was 878.9 g EtOH/kg catalyst/hr. The same reaction was performed with pure ethyl acetate as the feedstock, and the concentration of impurities are compared in Table 12. Reduction (%)=(wt % impurity with pure EtOAc−wt % impurity with mix feed)/(wt % impurity with pure EtOAc)*100

TABLE 12

| Impurity | Wt % (pure EtOAc) | Wt % (EtOAc—EtOH-water mix) | Reduction (%) |
|---|---|---|---|
| 2-Butanol | 1.499 | 0.778 | 48.1 |
| 1-Butanol | 0.415 | 0.124 | 70.1 |
| Heavies | 0.836 | 0.278 | 66.8 |
| average | — | — | 61.7 |
| EtOH selectivity | 81.8% | 91.8% | |

The following Examples 10 and 11 were prepared with ASPEN Plus 7.1 simulation software to test various feed composition and separation systems.

Example 10

Esterification Process

Fresh acetic acid and ethanol are fed to vaporizer along with recycle streams from the azeotrope column and hydrogenolysis purification of about 2.4:1.0 HOAc/EtOH. The vaporizer is operated at a pressure of about 260 to 290 kPa and at a temperature of 140° C. to produce a vapor stream comprising 65 wt. % acetic acid, 20.7 wt. % ethanol, 7.7 wt. % ethyl acetate and 6 wt. % water. The vapor stream is fed to a fixed bed reactor containing a strongly acidic catalyst; Amberlyst 36 ion-exchange resin. The reactor is operated at a pressure of about 260 to 290 kPa and at a temperature of 130° C. to 140° C.

An esterification product is withdrawn continuously from the reactor and is directly fed to an azeotrope column. The esterification product comprises 40 wt. % acetic acid, 1.6 wt. % ethanol, 44.3 wt. % ethyl acetate and 13.5 wt. % water. The azeotrope column operates at a base temperature of 130° C. to 140° C. and a pressure of about 260 to 290 kPa. A distillate comprising 88 wt. % ethyl acetate, 2.5 wt. % ethanol, and 9.48 wt. % water is condensed and biphasically separated using a decanter into an organic phase and an aqueous phase. The organic phase comprises 93.4 wt. % ethyl acetate, 2.6 wt. % ethanol and 3.9 wt. % water. The organic phase further comprises less than 0.005 wt. % acetic acid. The organic phase is refluxed to the azeotrope column and a portion of the organic phase is forwarded to the hydrogenolysis reactor as the ester feed stream.

The aqueous phase, which comprises 85.2 wt. % water, is fed to a recovery column. The distillate of the recovery column comprises organic components that are separated from the aqueous phase and are then fed back to the decanter. The residue of the recovery column is purged. The recovery column operates at a base temperature of 100° C. at atmospheric pressure.

A residue is withdrawn from the azeotrope column and recycled to the vaporizer. The residue comprises 84.2 wt. % acetic acid, 7.4 wt. % ethyl acetate, 6.6 wt. % water and 0.7 wt. % ethanol. In addition to the residue, a sidestream withdrawn near the base of the azeotrope column is also withdrawn and recycled to the vaporizer. The sidestream comprises 65.8 wt. % acetic acid, 20.1 wt. % ethyl acetate, 11.8 wt. % water, and 1.3 wt. % ethanol.

Example 11

Hydrogenolysis Process

A portion of the organic phase from Example 10 is fed along with hydrogen to a vaporizer in a hydrogenolysis process of about 13:1. A vapor feed stream is withdrawn from vaporizer and fed to a fixed bed reactor. Fixed bed reactor contains a copper-based catalyst. The fixed bed reactor operates at a temperate of 240° C. and a pressure of about 3,500 kPa. The conversion of ethyl acetate in the reactor is about 85%. A crude reaction mixture comprising 62.1 wt. % ethanol, 9.4 wt. % ethyl acetate, 2.6 wt. % water, 0.09 wt. % 2-butanol, 0.69 wt. % acetaldehyde, 0.02 wt. % diethyl acetal, and gases, such as hydrogen, carbon monoxide, carbon dioxide, and/or methane. The crude reaction mixture is fed to a flasher to remove the gases and the liquid portion thereof is fed to a light ends column.

The light ends column is operated at a base temperature of about 78° C. at atmospheric pressure. The distillate of the light ends column is recycled to the vaporizer of the hydrogenolysis process. The distillate comprises 63.8 wt. % ethyl acetate, 28.8 wt. % ethanol, 1.5 wt. % water, and 9.6 wt. % acetaldehyde. The residue comprises 95 wt. % ethanol, 0.15 wt. % 2-butanol, and 0.03 wt. % acetaldehyde. The residue of light ends column is withdrawn and fed to a finishing column. An ethanol product is withdrawn as a sidestream from a point above the feed point. The residue of the finishing column comprises 93% of the 2-butanol fed to the finishing column, along with a portion of the ethanol. The distillate of finishing columns comprises about 99% or more of the acetaldehyde fed to the finishing column. The ethanol product comprises 95.4 wt. % ethanol, 4.52 wt. % water, less than 0.01 wt. % acetaldehyde, and less than 0.01 wt. % 2-butanol.

About 50% of the ethanol product is separated and returned to the esterification reactor described in Example 10.

Example 12

Ethanol Product

Table 13 compares the ethanol product obtained from hydrogenolysis compared to fermentation, ethylene dehydrated, and acetic acid hydrogenation. Comparative A is a fermentation process that uses sugarcane and Comparative B is a fermentation process that uses molasses. Comparative C is a Fischer-Tropsch process. Comparative D is an acetic acid hydrogenation process. The ethanol product is shown as recovered using a finishing column and without a finishing column. The finishing column removes a significant amount of n-butanol and 2-butanol.

TABLE 13

| Component | Without finishing | With finishing | Fermentation A | B | C | D |
|---|---|---|---|---|---|---|
| Ethanol | 95.2 wt. % | 95.4 wt. % | 93.4 wt. % | 93.4 wt. % | 93.1 wt. % | 92.7 wt. % |
| Water | 4.5 wt. % | 4.5 wt. % | 6.6 wt. % | 6.5 wt. % | 6.9 wt. % | 7.4 wt. % |
| Acetic Acid | 47 wppm | 0 | 11 wppm | 10 wppm | 8 wppm | 14 wppm |
| Ethyl Acetate | 4 wppm | 2 wppm | 51 wppm | — | — | 70 wppm |
| Isopropanol | 394 wppm | 357 wppm | 2 wppm | 17 wppm | 10 wppm | 110 wppm |
| n-propanol | — | — | 238 wppm | 109 wppm | 121 wppm | 160 wppm |
| n-butanol | 413 wppm | 1 wppm | — | — | — | — |
| 2-butanol | 1548 wppm | 94 wppm | — | — | — | — |
| $C_4$ alcohols | 1961 wppm | 95 wppm | 35 wppm | 20 wppm | 17 wppm | 21 wppm |
| $C_5$ alcohols | — | — | 12 wppm | 11 wppm | 5 wppm | 0 |
| $C_{2+}$ alcohols | 2355 wppm | 452 wppm | 288 wppm | 156 wppm | 261 wppm | 291 wppm |
| Acetaldehyde | 0 | 0 | 29 wppm | 18 wppm | 4 wppm | 5 wppm |
| Methanol | — | — | 51 wppm | 42 wppm | 46 wppm | not detectable |

While the invention has been described in detail, modifications within the spirit and scope of the invention will be readily apparent to those of skill in the art. In view of the foregoing discussion, relevant knowledge in the art and references discussed above in connection with the Background and Detailed Description, the disclosures of which are all incorporated herein by reference. In addition, it should be understood that aspects of the invention and portions of various embodiments and various features recited herein and/or in the appended claims may be combined or interchanged either in whole or in part. In the foregoing descriptions of the various embodiments, those embodiments which refer to another embodiment may be appropriately combined with other embodiments as will be appreciated by one of skill in the art. Furthermore, those of ordinary skill in the art will appreciate that the foregoing description is by way of example only, and is not intended to limit the invention.

We claim:

1. A method of producing ethanol comprising:
   esterifying acetic acid and ethanol in a first reaction zone to produce an ester feed stream;
   reacting at least a portion of the ester feed stream with hydrogen in a second reaction zone to produce a crude reaction mixture comprising ethyl acetate, ethanol, and at least one alcohol having at least 4 carbon atoms;
   separating at least a portion of the crude reaction mixture in a first distillation column to yield a first distillate comprising ethyl acetate and a first residue comprising ethanol; and
   separating at least a portion of the first residue in a second distillation column to yield an ethanol sidestream and a second residue comprising the at least one alcohol having at least 4 carbon atoms.

2. The method of claim 1, wherein the ester feed stream comprises less than 6 wt. % ethanol and less than 5 wt. % water.

3. The method of claim 1, wherein the at least one alcohol having at least 4 carbon atoms is selected from the group consisting of n-butanol and 2-butanol.

4. The method of claim 1, wherein the crude reaction mixture comprises from 0.01 to 2 wt. % 2-butanol.

5. The method of claim 1, wherein the conversion of ethyl acetate to ethanol in the second reaction zone is from 50 to 95%.

6. The method of claim 1, wherein the conversion of ethyl acetate to ethanol in the second reaction zone is from 70 to 85%.

7. The method of claim 1, further comprising returning less than 60% of the ethanol sidestream to the first reaction zone.

8. The method of claim 1, wherein the second reaction zone comprises a copper-based catalyst.

9. The method of claim 1, wherein the second reaction zone comprises a Group VIII-based catalyst.

10. The method of claim 1, wherein the first residue comprises 92 wt. % to 97 wt. % ethanol, 3 wt. % to 8 wt. % water, 0.01 wt. % to 0.2 wt. % 2-butanol, and 0.02 wt. % to 0.08 wt. % isopropanol.

11. The method of claim 1, wherein the ethanol sidestream comprises 92 wt. % to 97 wt. % ethanol, 3 wt. % to 8 wt. % water, less than 0.1 wt. % 2-butanol, and 0.02 wt. % to 0.08 wt. % isopropanol.

12. A method of producing ethanol comprising:
   esterifying acetic acid and ethanol in a first reaction zone to produce an ester feed stream;

reacting at least a portion of the ester feed stream with hydrogen in a second reaction zone to produce a crude reaction mixture, wherein the conversion of ethyl acetate to ethanol is less than 85%;

separating at least a portion of the crude reaction mixture in a first distillation column to yield a first distillate comprising ethyl acetate and ethanol, and a first residue comprising ethanol; and returning at least a portion of the distillate to the second reaction zone.

13. The method of claim 12, further comprising separating at least a portion of the first residue in a second distillation column to yield an ethanol sidestream and a second residue comprising at least one alcohol having at least 4 carbon atoms.

14. The method of claim 13, further comprising returning a portion of the ethanol sidestream to the first reaction zone.

15. A method of producing ethanol comprising:
esterifying acetic acid and ethanol in a first reaction zone to produce an ester feed stream;
reacting at least a portion of the ester feed stream with hydrogen in a second reaction zone to produce a crude reaction mixture, wherein the conversion of ethyl acetate to ethanol is greater than 85%;
separating at least a portion of the crude reaction mixture in a first distillation column to yield a first distillate comprising ethyl acetate and ethanol, and a first residue comprising ethanol and at least one alcohol having at least 4 carbon atoms; and
returning at least a portion of the first distillate to the first reaction zone.

16. The method of claim 15, further comprising separating at least a portion of the first residue in a second distillation column to yield an ethanol sidestream and a second residue comprising the at least one alcohol having at least 4 carbon atoms.

17. The method of claim 16, further comprising returning a portion of the ethanol sidestream to the first reaction zone.

18. A method of producing ethanol comprising:
esterifying acetic acid and ethanol in a first reaction zone to produce an ester feed stream;
reacting at least a portion of the ester feed stream with hydrogen in a second reaction zone to produce a crude reaction mixture comprising ethanol, diethyl acetal, and at least one alcohol having at least 4 carbon atoms; and
separating at least a portion of the crude reaction mixture in one or more distillation columns to yield an ethanol product, wherein the ethanol product, based on the crude reaction mixture, has a reduced amount of diethyl acetal and a reduced amount of the at least one alcohol having at least 4 carbon atoms.

19. The method of claim 18, wherein the at least one alcohol having at least 4 carbon atoms is selected from the group consisting of n-butanol, and 2-butanol.

20. The method of claim 18, wherein the ethanol product comprises less than 0.1 wt. % of the at least one alcohol having at least 4 carbon atoms.

21. The method of claim 18, wherein the ethanol product comprises less than 0.01 wt. % diethyl acetal.

22. A method of producing ethanol comprising:
esterifying acetic acid and ethanol in a first reaction zone to produce an ester feed stream;
reacting at least a portion of the ester feed stream with hydrogen in a second reaction zone to produce a crude reaction mixture;
separating at least a portion of the crude reaction mixture in a first distillation column in the presence of an extractive agent to yield a first extractant stream comprising ethyl acetate and ethanol and a first residue comprising ethanol and the extractive agent; and
recovering ethanol from the first residue.

23. The method of claim 22, further comprising returning a portion of the first extractant stream to the first reaction zone.

24. The method of claim 22, further comprising returning a portion of the first extractant stream to the second reaction zone.

25. A method of producing ethanol comprising:
esterifying acetic acid and ethanol in a first reaction zone to produce an ester feed stream;
reacting at least a portion of the ester feed stream with hydrogen in a second reaction zone to produce a crude reaction mixture; and
separating at least a portion of the crude reaction mixture hydrogenation product in a first distillation column operated at a pressure of less than 101 kPa to yield a first distillate comprising ethyl acetate and ethanol and a residue comprising ethanol.

26. The method of claim 25, further comprising returning a portion of the first distillate to the first reaction zone.

27. The method of claim 25, further comprising returning a portion of the first distillate to the second reaction zone.

* * * * *